US012570979B2

(12) United States Patent
Thompson

(10) Patent No.: US 12,570,979 B2
(45) Date of Patent: Mar. 10, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/932,216

(22) Filed: Oct. 30, 2024

(65) Prior Publication Data

US 2025/0163426 A1     May 22, 2025

Related U.S. Application Data

(62) Division of application No. 18/518,069, filed on Nov. 22, 2023.

(51) Int. Cl.
*C12N 15/113* (2010.01)
*C12N 15/86* (2006.01)

(52) U.S. Cl.
CPC .......... *C12N 15/1137* (2013.01); *C12N 15/86* (2013.01); *C12N 2310/141* (2013.01); *C12N 2750/14143* (2013.01); *C12Y 207/01* (2013.01)

(58) Field of Classification Search
CPC .............. C12N 15/86; C12N 2310/141; C12N 2750/14143
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 * | 11/2021 | Minshull .............. | C12N 9/1241 |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |

FOREIGN PATENT DOCUMENTS

CA        2721333 A1    10/2009

OTHER PUBLICATIONS

Nature (2010. Gene Expression. Scitable. Available online at Nature. com. Accessed Dec. 16, 2024) (Year: 2010).*

NCBI Nucleotide Sequence ALK ligand. Search performed Dec. 26, 2024 (Year: 2023).*
NCBI Nucleotide Sequence ALK Receptor. Search performed Dec. 26, 2024 (Year: 2023).*
Denzler (et al. 2016. Impact of MicroRNA Levels, Target-Site Complementarity, and Cooperativity on Competing Endogenous RNA-Regulated Gene Expression. Molec. Cell. 64:565-579) (Year: 2016).*
Van den Berg (et al. 2016. Design of Effective Primary MicroRNA Mimics With Different Basal Stem Conformations. Molec. Ther. Nuc. Ac. 5:e278) (Year: 2016).*
Gorski (et al. 2017. RNA-based recognition and targeting: sowing the seeds of specificity. Nat. Rev. Molec. Cell. Biol. 18:215-228) (Year: 2017).*
Tritschler (et al. 2019. Concepts and limitations for learning developmental trajectories from single cell genomics. Development 146: dev170506) (Year: 2019).*
O'Brien, et al., Aug. 3, 2018, Front Endocrinol (Lausanne), 9:402, p. 1-12; Fig. 1; p. 2, "Biogenesis of miRNAs" (Year: 2018).*
Bottoni et al. "Targeting BTK through microRNA in chronic lymphocytic leukemia." Blood, The Journal of the American Society of Hematology 128.26 (2016): 3101-3112.
Brutons Tyrosine Kinase Genbank Sequence (Year: 2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Gen Bank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI Search results for SEQ ID No. 5 2024.
GenBank EGFR Sequence (2023).
Genbank FLT3 Sequence (2024).

(Continued)

*Primary Examiner* — Ram R Shukla
*Assistant Examiner* — Shabana S Meyering
(74) *Attorney, Agent, or Firm* — Gowling WLG (Canada) LLP

(57)        ABSTRACT

The embodiments of the present disclosure relate to decreasing the bioavailability of one or more target biomolecules by providing a composition that comprises a recombinant plasmid with one or more sequences of micro interfering ribonucleic acid (miRNA). When the recombinant plasmid interacts with a target cell, it causes the target cell to upregulate production of the miRNA, which then decreases the bioavailability of the target biomolecule. In some embodiments of the present disclosure, the target biomolecule is a kinase.

4 Claims, No Drawings

Specification includes a Sequence Listing.

(56) References Cited

OTHER PUBLICATIONS

NCBI Nucleotide Sequence for PARP, search performed Dec. 26, 2024 (2024).

Lam (et al. 2015. siRNA Versus miRNA as Therapeutics for Gene Silencing. Molec. Ther. Nuc. Ac. 4:e252) (Year: 2015).

Ying (et al. 2008. The MicroRNA (miRNA): Overview of the RNA Genes that Modulate Gene Function. Mol. Biotechnol. 38:257-268) (Year: 2008).

*Homo sapiens* VEGF, mRNA, NCBI Reference Sequence, version Oct. 2023, 9 pages, retrieved from the internet Jul. 2, 2025 (Year: 2023).

Pagliuca (et al. 2013. Analysis of the combined action of miR-143 and miR-145 on oncogenic pathways in colorectal cancer cells reveals a coordinate program of gene repression. Oncogene 32:4806-4813) (Year: 2013.

Fattore (et al. 2016. miR-579-3p controls melanoma progression and resistance to target therapy. PNAS 113 [34]:E5005-E5013) ( Year: 2016).

Origene (2024. Product datasheet for SC207797 B Raf [BRAF] [NM_004333] Human 3' UTR Clone. Rockville, MD: Origene) (Year: 2024).

NCBI (*Homo sapiens* B-Raf proto-oncogene, serine/threonine kinase [BRAF], transcript variants 1-2, 4-14, mRNA: [see reference for NM number]. Available online at NCBI.nlm.nih.gov. Accessed on May 16, 2025 (Year: 2025).

MiRbase (2025. "miR-143" and "miR-145", and "miR-579-3p". Available online at miRbase.org. Accessed on May 16, 2025) (Year: 2025).

Kondratov et al. "Direct head-to-head evaluation of recombinant adeno-associated viral vectors manufactured in human versus insect cells." Molecular Therapy 25.12 (2017): 2661-2675.

Wang et al. "Adeno-associated virus vector as a platform for gene therapy delivery". Nat Rev Drug Discov. May 2019; 18(5):358-378. (Year: 2019).

* cited by examiner

SEQUENCE LISTING

```
Sequence total quantity: 17
SEQ ID NO: 1              moltype = DNA   length = 5883
FEATURE                   Location/Qualifiers
source                    1..5883
                          mol_type = other DNA
                          organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctctttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcgccctg ctgccggctc tgcggcctct tccgcgtctt   540
cgccttcgcc ctcagacgag tcggatctcc ctttgggcg cctccccgcc taagcttatt   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gacccccaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaacccTat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggctttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
```

```
cgcttacaga caagctgtga ccgtctccgg gagctgcatg tgtcagaggt tttcaccgtc  2460
atcaccgaaa cgcgcgagac gaaagggcct cgtgatacgc ctattttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttaccca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtga   4740
agttccgcgt tacataactt acggtaaatg gcccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccacccc aattttgtat ttatttattt tttaattatt ttgtgcagcg atggggggcgg   5160
gggggggggg gggcgcgcgc caggcgggge ggggcgggge gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gcc                                                                  5883
```

SEQ ID NO: 2                moltype = DNA   length = 456
FEATURE                     Location/Qualifiers
source                      1..456
                            mol_type = other DNA
                            organism = synthetic construct
SEQUENCE: 2

```
gctagcatcg ataccgtcgc tatgtgctgg aggcttgctg aaggctgtat gctgtaaggt   60
ggttatggga gaatgccgtt ttggcctctg actacggca ttctcctaac caccttacag     120
gacacaaggc ctgttactag cactcacatg gaacaaatg ctctagcct ggaggcttgc      180
tgaaggctgt atgctgttga gtttcgcatt cttgttgccg ttttggcctc tgactgacgg   240
caacaagagc gaaactcaac aggacacaag gcctgttact agcactcaca tggaacaaat   300
ggcctctagc ctgaggcttg ctgaaggct gtatgctgtc tatcctttca agctagtcac     360
cgttttggc tctgactgac ggtgactagc gaaaggatag acaggacaca aggcctgtta     420
ctagcactca catggaacaa atggcctctc tagaat                              456
```

SEQ ID NO: 3                moltype = DNA   length = 456
FEATURE                     Location/Qualifiers
source                      1..456
                            mol_type = other DNA -continued

```
                       organism = synthetic construct
SEQUENCE: 3
gctagcatcg ataccgtcgc tatgtgctgg aggcttgctg aaggctgtat gctgaagtta    60
gcatgtgtcc cagaaccgtt ttggcctctg actgacggtt ctgggacatg ctaacttcag   120
gacacaaggc ctgttactag cactcacatg gaacaaatgg cctctagcct ggaggcttgc   180
tgaaggctgt atgctgagaa gaaaggtatc ccaattgccg ttttggcctc tgactgacgg   240
caattgggac ctttcttctc aggacacaag gcctgttact agcactcaca tggaacaaat   300
ggcctctagc ctggaggctt gctgaaggct gtatgctgta gtgtttccaa atactgcttg   360
cgttttggcc tctgactgac gcaagcagta tggaaacact acaggacaca aggcctgtta   420
ctagcactca catggaacaa atggcctctc tagaat                             456

SEQ ID NO: 4             moltype = DNA   length = 456
FEATURE                  Location/Qualifiers
source                   1..456
                         mol_type = other DNA
                         organism = synthetic construct
SEQUENCE: 4
gctagcatcg ataccgtcgc tatgtgctgg aggcttgctg aaggctgtat gctgtctgac    60
agtgatgtca tcctttcgtt ttggcctctg actgacgaaa ggatgatcac tgtcagacag   120
gacacaaggc ctgttactag cactcacatg gaacaaatgg cctctagcct ggaggcttgc   180
tgaaggctgt atgctgattt aggtcagatg gaaactcgcg ttttggcctc tgactgacgc   240
gagtttccct gacctaaatc aggacacaag gcctgttact agcactcaca tggaacaaat   300
ggcctctagc ctggaggctt gctgaaggct gtatgctgag tgtatgctta acgtggactt   360
cgttttggcc tctgactgac gaagtccacg aagcatacac tcaggacaca aggcctgtta   420
ctagcactca catggaacaa atggcctctc tagaat                             456

SEQ ID NO: 5             moltype = DNA   length = 456
FEATURE                  Location/Qualifiers
source                   1..456
                         mol_type = other DNA
                         organism = synthetic construct
SEQUENCE: 5
gctagcatcg ataccgtcgc tatgtgctgg aggcttgctg aaggctgtat gctgatactt    60
cagcctgaat cgtgtgaccgtt ttggcctctg actgacggtc acgattggct gaagtatcag  120
gacacaaggc ctgttactag cactcacatg gaacaaatgg cctctagcct ggaggcttgc   180
tgaaggctgt atgctgactt cactcatatt gttccactcg ttttggcctc tgactgacga   240
gtggaacaat gagtgaagtc aggacacaag gcctgttact agcactcaca tggaacaaat   300
ggcctctagc ctggaggctt gctgaaggct gtatgctgta tattctacaa atcaccaggg   360
cgttttggcc tctgactgac gccctggtga tgtagaatat acaggacaca aggcctgtta   420
ctagcactca catggaacaa atggcctctc tagaat                             456

SEQ ID NO: 6             moltype = DNA   length = 456
FEATURE                  Location/Qualifiers
source                   1..456
                         mol_type = other DNA
                         organism = synthetic construct
SEQUENCE: 6
gctagcatcg ataccgtcgc tatgtgctgg aggcttgctg aaggctgtat gctgtataag    60
tccagtgaga agaaggcgtt ttggcctctg actgacgcct cttctctgg acttatacag    120
gacacaaggc ctgttactag cactcacatg gaacaaatgg cctctagcct ggaggcttgc   180
tgaaggctgt atgctgctat catcaaatga gctgctgcgt tttggcctct gactgacgca   240
gcagctcttg atgatagtca ggacacaagg cctgttacta gcactcacat ggaacaaatg   300
gcctctagcc tggaggcttg ctgaaggctg tatgctgaag actgctggaa attctatggc   360
tgttttggcc tctgactgac gaccatagaa tccagcagtc tcaggacaca aggcctgtta   420
ctagcactca catggaacaa atggcctctc tagaat                             456

SEQ ID NO: 7             moltype = DNA   length = 457
FEATURE                  Location/Qualifiers
source                   1..457
                         mol_type = other DNA
                         organism = synthetic construct
SEQUENCE: 7
gctagcatcg ataccgtcgc tatgtgctgg aggcttgctg aaggctgtat gctgattagc    60
actggtgatt tccggctgtt ttggcctctg actgacgacc ggaaatccag tgctaatcag   120
gacacaaggc ctgttactag cactcacatg gaacaaatgg cctctagcct ggaggcttgc   180
tgaaggctgt atgctgattg agtttcgcat tcttgttgcc gttttggcct ctgactgacg   240
gcaacaagag cgaaactcaa caggacacaa ggcctgttac tagcactcac atggaacaaa   300
tggcctctag cctggaggct tgctgaaggc tgtatgctga ttgatcaggc aaacatagtc   360
ccgttttggc ctctgactga cgggactatg tgcctgatca atcaggacac aaggcctgtt   420
actagcactc acatggaaca aatggcctct ctagaat                            457

SEQ ID NO: 8             moltype = DNA   length = 456
FEATURE                  Location/Qualifiers
source                   1..456
                         mol_type = other DNA
                         organism = synthetic construct
SEQUENCE: 8
gctagcatcg ataccgtcgc tatgtgctgg aggcttgctg aaggctgtat gctgtctgat    60
cgtggtgtta tttgggcgtt ttggcctctg actgacgccc aaataaccac gatcagacag   120
```

```
gacacaaggc ctgttactag cactcacatg gaacaaatgg cctctagcct ggaggcttgc   180
tgaaggctgt atgctgttga gtttcgcatt cttgttgccg ttttggcctc tgactgacgg   240
caacaagagc gaaactcaac aggacacaag gcctgttact agcactcaca tggaacaaat   300
ggcctctagc ctggaggctt gctgaaggct gtatgctgta tcctcttata actcagcctc   360
cgttttggct tctgactgac ggaggctgag ataagaggac acaggacaca aggcctgtta   420
ctagcactca catggaacaa atggcctctc tagaat                             456
```

```
SEQ ID NO: 9                moltype = DNA   length = 456
FEATURE                     Location/Qualifiers
source                      1..456
                            mol_type = other DNA
                            organism = synthetic construct
SEQUENCE: 9
gctagcatcg ataccgtcgc tatgtgctgg aggcttgctg aaggctgtat gctgtcgtac   60
tgacttgtag gtatgccgtt ttggcctctg actgacggca tacctaagtc agtacgtcag   120
gacacaaggc ctgttactag cactcacatg gaacaaatgg cctctagcct ggaggcttgc   180
tgaaggctgt atgctgactc ctaatcaata gcttccaccg ttttggcctc tgactgacgg   240
tggaagcttg attaggagtc aggacacaag gcctgttact agcactcaca tggaacaaat   300
ggcctctagc ctggaggctt gctgaaggct gtatgctgaa tatgccttta agctttgctg   360
cgttttggcc tctgactgac gcagcaaagc aaaggcatat tcaggacaca aggcctgtta   420
ctagcactca catggaacaa atggcctctc tagaat                             456
```

```
SEQ ID NO: 10               moltype = DNA   length = 6339
FEATURE                     Location/Qualifiers
source                      1..6339
                            mol_type = other DNA
                            organism = synthetic construct
SEQUENCE: 10
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctctttta tgaggagttg   180
tggcccgttg tcaggcaacg tggcgtggtg tgcactgtgt ttgctgacgc aaccccact   240
ggttggggca ttgccaccac ctgtcagctc ctttccggga ctttcgcttt cccctcct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgcggg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa cacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctcctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataacc    2640
ctgataaatg cttcaataat attgaaaaag gaagagtatg agtattcaac atttccgtgt   2700
cgcccttatt cccttttttg cggcattttg ccttcctgt tttgctcacc cagaaacgct   2760
ggtgaaagta aaagatgctg aagatcagt gggtgcacga gtggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
```

```
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacg acgggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatcccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg ggggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg ccccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccc   5100
ccccaccccc aattttgtat ttatttattt tttaattatt ttgtgcagcg atggggggcgg   5160
gggggggggg gggcgcgcgc caggcggggc ggggcggggc gagggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct aggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcgggactg ctgtgcctga cttggctcca ggagggctcc   5880
gccgctagca tcgataccgt cgctatgtgc tggaggcttg ctgaaggctg tatgctgtaa   5940
ggtggttatg ggagaatgcc gttttggcct ctgactacg gcattctcct aaccacctta   6000
caggacacaa ggcctgttac tagcactcac atggaacaaa tggcctctag cctgaggct   6060
tgctgaaggc tgtatgctgt tgagtttcgc attcttgttg ccgttttggc tctgactagca   6120
cggcaacaag agcgaaactc aacaggacac aaggcctgtt actagcactc acatggaaca   6180
aatggcctct agcctggagg cttgctgaag gctgtatgct gtctatcctt tcaagctagt   6240
caccgttttg gcctctgact gacggtgact agcgaaagga tagacaggac acaaggcctg   6300
ttactagcac tcacatggaa caaatggcct ctctagaat                         6339
```

```
SEQ ID NO: 11         moltype = DNA  length = 6339
FEATURE               Location/Qualifiers
source                1..6339
                      mol_type = other DNA
                      organism = synthetic construct
SEQUENCE: 11
aatcaacctc tggattacaa aatttgtgaa agattgactg gtattcttaa ctatgttgct   60
cctttacgc tatgtggata cgctgcttta atgcctttgt atcatgctat tgcttccgt    120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgtct   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
```

-continued

```
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta caggggcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgga   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccc   5100
cccaccccc aattttgtat ttatttattt tttaattatt ttgtgcagcg atgggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggctttg cccgggcggc   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgtttc   5760
```

```
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgaag   5940
ttagcatgtg tcccagaacc gttttggcct ctgactgacg gttctgggac atgctaactt   6000
caggacacaa ggcctgttac tagcactcac atggaacaaa tggcctctag cctggaggct   6060
tgctgaaggc tgtatgctga aagaaaggt atcccaattg ccgtttggcc tctctgactga   6120
cggcaattgg gacctttctt ctcaggacac aaggcctgtt actagcactc acatggaaca   6180
aatggcctct agcctggagg cttgctgaag gctgtatgct gtagtgtttc caaatactgc   6240
ttgcgttttg gcctctgact gacgcaagca gtatggaaac actacaggac acaaggcctg   6300
ttactagcac tcacatggaa caaatggcct ctctagaat   6339
```

```
SEQ ID NO: 12              moltype = DNA   length = 6339
FEATURE                    Location/Qualifiers
source                     1..6339
                           mol_type = other DNA
                           organism = synthetic construct
SEQUENCE: 12
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc ctgccgtctt ggccgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cactttaaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactgg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
```

```
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctga gcgctcgctc gctcactgag   4560
gccgccccgg caaagcccgg gcgtcggggc acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg ccccgcctgg ctgaccgcgc aacgaccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg   5160
ggggggggg gggcgcgcgc caggcggggc ggggcggggc gaggggcggg gcggggcgag   5220
gcggagaggt gcggcggcag ccaatcagag cggcggcctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccagta tcagcagaag gacatttttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtct   5940
gacagtgatg tcatccttc gttttggcct ctgactgacg aaaggatgat cactgtcaga   6000
caggacacaa ggcctgttac tagcactcac atggaacaaa tggcctctag cctggaggct   6060
tgctgaaggc tgtatgctga tttaggtcag atggaaactc gcgtttggc ctctgactga   6120
cgcgagtttc cctgacctaa atcaggacac aaggcctgtt actagcactc acatggaaca   6180
aatggcctct agcctggagg cttgctgaag gctgtatgct gagtgtatgc ttaacgtgga   6240
cttcgttttg gcctctgact gacgaagtcc acgaagcata cactcaggac acaaggcctg   6300
ttactagcac tcacatggaa caaatggcct ctctagaat                          6339
```

SEQ ID NO: 13         moltype = DNA  length = 6339
FEATURE               Location/Qualifiers
source                1..6339
                      mol_type = other DNA
                      organism = synthetic construct
SEQUENCE: 13

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctctta tgaggagttg   180
tggcccgttg tcaggcaacg tggcgtggtg tgcactgtgt ttgctgacgc aaccccact   240
ggttgggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtcct tcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa   720
actcatcaat gtatcttatc atgtctggat ctcgacctcg agagaccat cgctacgtag   780
ataagtagca tggcgggtta tcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgc   1320
ctgtagcggc gcattaagcg cggcgggtgt ggtggttacg cgcagcgtga ccgctacact   1380
tgccagcggc ctagcgcccg ctcctttcgc tttcttccct tcctttctcg ccacgttcgc   1440
cggctttccc cgtcaagctc taaatcgggg ctcccttta gggttccgat ttagtgcttt   1500
acggcacctc gaccccaaaa aacttgatta gggtgatggt tcacgtagtg gccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
```

-continued

```
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcta aaaattttta tccttgcgtt    2100
gaaataaagg cttctcccgc aaaagtatta cagggtcata atgttttttgg tacaaccgat    2160
ttagctttat gctctgaggc tttattgctt aattttgcta attctttgcc ttgcctgtat    2220
gatttattgg atgttggaat tcctgatgcg gtatttttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctatttttat aggttaatgt    2520
catgataata atggtttctt agacgtcagg tggcactttt cggggaaatg tgcgcggaac    2580
ccctatttgt ttatttttct aaatacattc aaatatgtat ccgctcatga gacaataacc    2640
ctgataaatg cttcaataat attgaaaaag gaagagtatg agtattcaac atttccgtgt    2700
cgcccttatt ccctttttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
actcggtcgc cgcatacact attctcagaa tgacttggtt gagtactcac cagtcacaga    3000
aaagcatctt acggatggca tgacagtaag agaattatgc agtgctgcca taaccatgag    3060
tgataacact gcggccaact tacttctgac aacgatcgga ggaccgaagg agctaaccgc    3120
ttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat taatagactg    3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctacacg acggggagtc aggcaactat    3480
ggatgaacga aatagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc tttttgataa tctcatgacc aaaatccctt aacgtgagtt    3660
ttcgttccac tgagcgtcag accccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct acaccgaact    4080
gagataccta cagcgtgagc tatgagaaag cgccacgctt cccgaaggga gaaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggcctttttt    4320
acggttcctg gccttttgct ggccttttgc tcacatgttc tttcctgcgt tatccccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagttt    4740
agttccgcgt tacataactt acggtaaatg gcccgcctgg ctgaccgccc aacgacccccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccccct    5100
ccccaccccc aattttgtat ttatttattt tttaattatt ttgtgcagcg atggggggcgg    5160
ggggggggggg gggcgcgcgc caggcggggc ggggcggggc gaggggcggg gcggggcgag    5220
gcggagaggt gcggcgcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aacccccagta tcagcagaag gacattttag gacgggactt gggtgactct agggcactgg    5640
ttttcttttcc agagagcgga acaggcgagg aaaagtagtc ccttctcggc gattctgcgg    5700
agggatctcc gtgggggcgt gaacgccgat gatgcctcta ctaaccatgt tcatgttttc    5760
ttttttttttc tacaggtcct gggtgacgaa caggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgata    5940
cttcagcctg aatcgtgacc gtttttggcct ctgactgacg gtcacgattg ctgaagtat    6000
caggacacaa ggcctgttac tagcactcac atggaacaaa tggcctctag cctggaggct    6060
tgctgaaggc tgtatgctga cttcactcat attgttccac tcgttttggc ctctgactga    6120
cgagtcggaac aatgagtgaa gtcaggcacac aaggcctgtt actagcactc acatggaaca    6180
aatgccctct agcctggagg cttgctgaag gctgtatgct gtatattcta caaatcacca    6240
gggcgttttg gcctctgact gacgccctgg tgatgtagaa tatacaggac acaaggcctg    6300
ttactagcac tcacatggaa caaatggcct ctctagaat              6339
```

-continued

```
SEQ ID NO: 14          moltype = DNA   length = 6339
FEATURE                Location/Qualifiers
source                 1..6339
                       mol_type = other DNA
                       organism = synthetic construct
SEQUENCE: 14
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaacctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt aaaaatatat gagggttcta aaaatttttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga dacaataacc   2640
ctgataaatg cttcaataat attgaaaaag gaagagtatg agtattcaac atttccgtat   2700
cgcccttatt ccctttttttg cggcatttttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttttt   4320
acggttcctg gccttttgct ggccttttgc tcacatgttc tttcctgcgt tatcccctga   4380
```

-continued

```
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctcccgcg  cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc  aattttgtat ttatttattt tttaattatt ttgtgcagcg atggggggcgg   5160
ggggggggcgg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttc  tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtat   5940
aagtccagtg agaagaaggc gttttggcct ctgactgacg ccttcttctc tggacttata   6000
caggacacaa ggcctgttac tagcactcac atggaacaaa tggcctctag cctgaggct   6060
tgctgaaggc tgtatgctgc tatcatcaaa tgagctgctg cgttttggcc tctgactgac   6120
gcagcagctc ttgatgatag tcaggacaca aggcctgtta ctagcactca catggaacaa   6180
atggcctcta gcctgaggc ttgctgaagg ctgtatgctg aagactgctg gaaattctat   6240
ggctgttttg gcctctgact gacgaccata gaatccagca gtctcaggac acaaggcctg   6300
ttactagcac tcacatggaa caaatggcct ctctagaat                          6339
```

```
SEQ ID NO: 15          moltype = DNA  length = 6340
FEATURE                Location/Qualifiers
source                 1..6340
                       mol_type = other DNA
                       organism = synthetic construct
SEQUENCE: 15
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt cccctccct   300
attgccacgt cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggc accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gaattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ccggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
```

```
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttattttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccaccccc aattttgtat ttatttattt tttaattatt ttgttgcagcg atgggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctccg   5400
actgaccgcg ttactaaaac aggtaagtcc ggcctccgcg ccgggtttg gcgcctcccg   5460
cgggcgcccc cctcctcacg cgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcagtgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgctgc cttggctcca ggagggctcc   5880
gccgctagca tcgataccgt cgctatgtgc tggaggctg ctgaaggctg tatgctgatt   5940
agcactggtg atttccggct gttttggcct ctgactgacg accggaaatc cagtgctaat   6000
caggacacaa ggcctgttac tagcactcac atggaacaaa tggcctctag cctggaggct   6060
tgctgaaggc tgtatgctga ttgagtttcg cattcttgtt gccgtttggg cctctgactg   6120
acggcaacaa gagcgaaact caacaggaca caaggcctac tagcact cacatggacat   6180
aaatggcctc tagcctggag gcttgctgaa ggctgtatgc tgattgatca ggcaaacata   6240
gtcccgtttt ggcctctgac tgacgggact atgtgcctga tcaatcagga cacaaggcct   6300
gttactagca ctcacatgga acaaatggcc tctctagaat                         6340
```

```
SEQ ID NO: 16          moltype = DNA   length = 6339
FEATURE                Location/Qualifiers
source                 1..6339
                       mol_type = other DNA
                       organism = synthetic construct
SEQUENCE: 16
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct   300
```

-continued

```
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaaatg  660
catcacaaat ttcacaaata aagcatttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgcc ctagcgcccg ctcctttcgc tttcttccct tcctttctcg ccacgttcgc 1440
cggctttccc cgtcaagctc taaatcgggg gctcccttta gggttccgat ttagtgcttt 1500
acggcacctc gaccccaaaa aacttgatta gggtgatggt tcacgtagtg ggccatcgcc 1560
ctgatagacg gtttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
catattgatg gtgatttgac tgtctccggc ctttctcacc cgtttgaatc tttacctaca 2040
cattactcag gcattgcatt taaaatatat gagggttcta aaaatttta tccttgcgtt 2100
gaaataaagg cttctcccgc aaaagtatta cagggtcata atgttttggg tacaaccgat 2160
ttagctttat gctctgaggc tttattgctt aattttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctattttat aggttaatgt 2520
catgataata atggtttctt agacgtcagg tggcactttt cggggaaatg tgcgcggaac 2580
ccctatttgt ttatttttct aaatacattc aaatatgtat ccgctcatga gacaataacc 2640
ctgataaatg cttcaataat attgaaaaag gaagagtatg agtattcaac atttccgtgt 2700
cgcccttatt ccctttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
tttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagataccta cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggccttttt 4320
acggttcctg gccttttgct ggccttttgc tcacatgttc tttcctgcgt tatccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctcccgcg cgttggccga ttcattaatg cagcagctgc gcgctcgctc gctcactgag 4560
gccgcccggg caaagcccgg gcgtcgggcg acctttggtc gcccggcctc agtgagcgag 4620
cgagcgcgca gagagggagt ggccaactcc atcactaggg gttccttgta gttaatgatt 4680
aacccgccat gctacttatc tacgtagcca cattgattat tgactagtga 4740
agttccgcgt tacataactt acggtaaatg gcccgcctgg ctgaccgccc aacgaccccc 4800
gcccattgac gtcaataatg acgtatgttc ccatagtaac gccaataggg actttccatt 4860
gacgtcaatg ggtggagtat ttacggtaaa ctgcccactt ggcagtacat caagtgtatc 4920
atatgccaag tacgcccct attgacgtca atgacgtaa atggcccgcc tggcattatg 4980
cccagtacat gaccttatgg gactttccta cttggcagta catctacgta ttagtcatcg 5040
```

```
ctattaccat ggtcgaggtg agccccacgt tctgcttcac tctccccatc tcccccccct   5100
ccccaccccc aattttgtat ttatttattt tttaattatt ttgtgcagcg atggggggcgg   5160
ggggggggg gggcgcgcgc caggcggggc ggggcggggc gagggcggg gcggggcgag   5220
gcggagaggt gcggcggcag ccaatcagag cggcgcgctc cgaaagtttc cttttatggc   5280
gaggcggcgg cggcggcgcg cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctc ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgtttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtct   5940
gatcgtggtg ttatttgggc gttttggcct ctgactgacg cccaaataac cacgatcaga   6000
caggacacaa ggcctgttac tagcactcac atggaacaaa tggcctctag cctggaggct   6060
tgctgaaggc tgtatgctgt tgagtttcgc attcttgttg ccgtttttgc ctctgactga   6120
cggcaacaag agcgaaactc aacaggacac aaggcctgtt actagcactc acatggaaca   6180
aatggcctct agcctggagg cttgctgaag gctgtatgct gtatcctctt ataactcagc   6240
ctccgttttg gcctctgact gacgaggct gagataagag gatacaggac acaaggcctg   6300
ttactagcac tcacatggaa caaatggcct ctctagaat   6339
```

SEQ ID NO: 17          moltype = DNA   length = 6339
FEATURE                Location/Qualifiers
source                 1..6339
                       mol_type = other DNA
                       organism = synthetic construct
SEQUENCE: 17
```
aatcaacctc tggattacaa aatttgtgaa agattgactg gtattcttaa ctatgttgct   60
...
actcggtcgc cgcatacact attctcagaa tgacttggtt gagtactcac cagtcacaga   3000
```

-continued

```
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
cccccacccc aattttgtat ttatttattt tttaattatt ttgtgcagcg atggggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcggggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggtttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacatttttag gacgggactt gggtgactct agggcactgg   5640
ttttctttcc agagagcgga acaggcgagg aaaagtagtc ccttctcggc gattctgcgg   5700
agggatctct gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtcg   5940
tactgacttg taggtatgcc gttttggcct ctgactgacg gcatacctaa gtcagtacgt   6000
caggacacaa ggcctgttac tagcactcac atggaacaaa tggcctctag cctggaggct   6060
tgctgaaggc tgtatgctga ctcctaatca atagcttcca ccgttttggc ctctgactga   6120
cggtggaagc ttgattagga gtcaggacac aaggcctgtt actagcactc acatggaaca   6180
aatgcctct agcctggagg cttgctgaag gctgtatgct gaatatgcct ttaagctttg   6240
ctgcgttttg gcctctgact gacgcagcaa agcaaaggca tattcaggac acaaggcctg   6300
ttactagcac tcacatggaa caaatggcct ctctagaat                         6339
```

COMPOSITION FOR REGULATING PRODUCTION OF INTERFERING RIBONUCLEIC ACID

CROSS REFERENCE TO RELATED APPLICATION

The present application is a division of U.S. patent application Ser. No. 18/518,069 filed Nov. 22, 2023, entitled "Composition For Regulating Production Of Interfering Ribonucleic Acid" currently pending, the entirety of which is incorporated herein by reference.

SEQUENCE LISTING

This application contains a Sequence Listing electronically submitted via Patent Center to the United States Patent and Trademark Office as an XML Document file entitled "A8149358US-Sequence Listing.xml" created on 2023 Nov. 17 and having a size of 75,546 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA that will suppress over-expression or mis-expression of kinases.

BACKGROUND

Bioactive molecules, including kinases, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro interfering ribonucleic acid (miRNA). The sequences of miRNA may be complementary to a sequence of target messenger RNA (mRNA) that encodes for translation of a target biomolecule and the miRNA can cause the bioavailability of the target mRNA to decrease because it is degraded or inactivated by the miRNA, thereby causing a decrease in bioavailability of the target biomolecule within a subject that is administered the one or more compositions. In some embodiments of the present disclosure, the target biomolecule is a cytokine. In some embodiments of the present disclosure, the target biomolecule is a cytokine such as IL-1beta. In some embodiments of the present disclosure, the target biomolecule is a cytokine such as IL-18. In some embodiments of the present disclosure, the target biomolecule is a cytokine such as IL-6. In some embodiments of the present disclosure, the target biomolecule is a cytokine such as IL-17A. In some embodiments of the present disclosure, the target biomolecule is a cytokine such as interferon gamma. In some embodiments of the present disclosure, the target biomolecule is a cytokine such as IL-2. In some embodiments of the present disclosure, the target biomolecule is a cytokine such as IL-4. In some embodiments of the present disclosure, the target biomolecule is a cytokine such as IL-5. In some embodiments of the present disclosure, the target biomolecule is a cytokine such as IL-10. In some embodiments of the present disclosure, the target biomolecule is a cytokine such as IL-22.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of Bruton's tyrosine kinase.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets mRNA of EGF.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets mRNA of VEGF.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets mRNA of BRAF.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets mRNA of ALK.

Some embodiments of the present disclosure relate to a recombinant plasmid. In some embodiments of the present disclosure, the RP comprises a nucleotide sequence of SEQ ID NO. 1 and SEQ ID NO. 7. The RP comprises a nucleotide sequence encoding one or more nucleotide sequences encoding a miRNA sequence that targets mRNA of HER.

Some embodiments of the present disclosure relate to a recombinant plasmid. In some embodiments of the present disclosure, the RP comprises a nucleotide sequence of SEQ ID NO. 1 and SEQ ID NO. 8. The RP comprises a nucleotide sequence encoding one or more nucleotide sequences encoding a miRNA sequence that targets mRNA of FLT3.

Some embodiments of the present disclosure relate to a recombinant plasmid. In some embodiments of the present disclosure, the RP comprises a nucleotide sequence of SEQ ID NO. 1 and SEQ ID NO. 9. The RP comprises a nucleotide sequence encoding one or more nucleotide sequences encoding a miRNA sequence that targets mRNA of PARP.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, or SEQ ID NO. 9, to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example Bruton's tyrosine kinase. A first approach utilizes gene vectors containing nucleotide sequences for increasing the endogenous production of one or more sequences of miRNA, which are complete or partial sequences and/or combinations thereof, that target and silence the mRNA of Bruton's tyrosine kinase, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example EGF. A first approach utilizes gene vectors containing nucleotide sequences for increasing the endogenous production of one or more sequences of miRNA, which are complete or partial sequences and/or combinations thereof, that target and silence the mRNA of EGF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example VEGF. A first approach utilizes gene vectors containing nucleotide sequences for increasing the endogenous production of one or more sequences of miRNA, which are complete or partial sequences and/or combinations thereof, that target and silence the mRNA of VEGF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example BRAF. A first approach utilizes gene vectors containing nucleotide sequences for increasing the endogenous production of one or more sequences of miRNA, which are complete or partial sequences and/or combinations thereof, that target and silence the mRNA of BRAF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example ALK. A first approach utilizes gene vectors containing nucleotide sequences for increasing the endogenous production of one or more sequences of miRNA, which are complete or partial sequences and/or combinations thereof, that target and silence the mRNA of ALK, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example HER. A first approach utilizes gene vectors containing nucleotide sequences for increasing the endogenous production of one or more sequences of miRNA, which are complete or partial sequences and/or combinations thereof, that target and silence the mRNA of HER, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example FLT3. A first approach utilizes gene vectors containing nucleotide sequences for increasing the endogenous production of one or more sequences of miRNA, which are complete or partial sequences and/or combinations thereof, that target and silence the mRNA of FLT3, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PARP. A first approach utilizes gene vectors containing nucleotide sequences for increasing the endogenous production of one or more sequences of miRNA, which are complete or partial sequences and/or combinations thereof, that target and silence the mRNA of PARP, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a kinase that is found within a subject. A biomolecule may be endogenous or exogenous to a subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is Bruton's tyrosine kinase.

In some embodiments of the present disclosure, the target biomolecule is EGF.

In some embodiments of the present disclosure, the target biomolecule is VEGF.

In some embodiments of the present disclosure, the target biomolecule is BRAF.

In some embodiments of the present disclosure, the target biomolecule is ALK.

In some embodiments of the present disclosure, the target biomolecule is HER.

In some embodiments of the present disclosure, the target biomolecule is FLT3.

In some embodiments of the present disclosure, the target biomolecule is PARP.

In some embodiments of the present disclosure, the insert comprises one or more nucleotide sequences that each encode one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as IL-1beta, IL-18, IL-6, IL-17A, interferon gamma, IL-2, IL-4, IL-5, IL-10, or IL-22. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as IL-1beta, IL-18, IL-6, IL-17A, interferon gamma, IL-2, IL-4, IL-5, IL-10, or IL-22. Increased endogenous expression of the one or more miRNA sequences results in a decreased bioavailability of the desired biomolecule, which may also be referred to as a target biomolecule.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ $TCID_{50}$/kg (50% tissue culture infective dose per kilogram of the patient's body mass. In some embodiments of the present disclosure, the therapeutically effective amount of the composition that is administered to the patient is about $1 \times 10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with examples being Bruton's tyrosine kinase, EGF, VEGF, BRAF, ALK, HER, FLT3, or PARP. The RP is comprised of AAV2 inverted terminal repeats (ITRs), a composite CASI promoter, a human growth hormone (HGH) signal peptide followed by a miRNA expression cassette containing up to six different miRNAs targeting Bruton's tyrosine kinase, EGF, VEGF, BRAF, ALK, HER, FLT3, or PARP, followed by a Woodchuck Hepatitis Virus post-transcriptional regulatory element (WPRE) and an SV40 polyA signal.

SEQ ID NO. 1 (backbone sequence No. 1):

5' aatcaacctctggattacaaaatttgtgaaagattgactggtattcttaactatgttg ctccttttacgctatgtggatacgctgctttaatgcctttgtatcatgctattgcttcccg tatggctttcattttctcctccttgtataaatcctggttgctgtctctttatgaggagttg tggcccgttgtcaggcaacgtggcgtggtgtgcactgtgtttgctgacgcaaccccact ggttggggcattgccaccacctgtcagctcctttccgggactttcgctttcccctccct attgccacggcggaactcatcgccgcctgccttgcccgctgctggacaggggctcggctg ttgggcactgacaattccgtggtgttgtcggggaaatcatcgtcctttccttggctgctc gcctgtgttgccacctggattctgcgcgggacgtccttctgctacgtcccttcggccctc aatccagcggaccttccttcccgcggcctgctgccggctctgcggcctcttccgcgtctt -continued

```
cgccttcgccctcagacgagtcggatctccctttgggccgcctccccgcctaagcttatc gataccgtcgagatctaacttgtttattgcagcttataatggttacaaataaagcaatag catcacaaatttcacaaataaagcattttttttcactgcattctagttgtggtttgtccaa actcatcaatgtatcttatcatgtctggatctcgacctcgactagagcatggctacgtag ataagtagcatggcgggttaatcattaactacaaggaacccctagtgatggagttggcca ctccctctctgcgcgctcgctcgctcactgaggccgggcgaccaaaggtcgcccgacgcc cgggctttgcccgggcggcctcagtgagcgagcgagcgcgcagctggcgtaatagcgaag aggcccgcaccgatcgcccttcccaacagttgcgcagcctgaatggcgaatggcgattcc gttgcaatggctggcggtaatattgttctggatattaccagcaaggccgatagtttgagt tcttctactcaggcaagtgatgttattactaatcaaagaagtattgcgacaacggttaat ttgcgtgatggacagactcttttactcggtggcctcactgattataaaaacacttctcag gattctggcgtaccgttcctgtctaaaatccctttaatcggcctcctgtttagctcccgc tctgattctaacgaggaaagcacgttatacgtgctcgtcaaagcaaccatagtacgcgcc ctgtagcggcgcattaagcgcggcgggtgtggtggttacgcgcagcgtgaccgctacact tgccagcgccctagcgcccgctcctttcgctttcttcccttcctttctcgccacgttcgc cggctttccccgtcaagctctaaatcggggggctccctttagggttccgatttagtgcttt acggcacctcgaccccaaaaaacttgattagggtgatggttcacgtagtgggccatcgcc ctgatagacggtttttcgccctttgacgttggagtccacgttctttaatagtggactctt gttccaaactggaacaacactcaaccctatctcggtctattcttttgatttataagggat tttgccgatttcggcctattggttaaaaaatgagctgatttaacaaaaatttaacgcgaa ttttaacaaaatattaacgtttacaatttaaatatttgcttatacaatcttcctgtttttt ggggcttttctgattatcaaccggggtacatatgattgacatgctagttttacgattacc gttcatcgattctcttgtttgctccagactctcaggcaatgacctgatagcctttgtaga gacctctcaaaaatagctaccctctccggcatgaatttatcagctagaacggttgaatat catattgatggtgatttgactgtctccggcctttctcacccgtttgaatctttacctaca cattactcaggcattgcatttaaaatatatgagggttctaaaaattttttatccttgcgtt gaaataaaggcttctcccgcaaaagtattacagggtcataatgttttttggtacaaccgat ttagctttatgctctgaggctttattgcttaattttgctaattctttgccttgcctgtat gatttattggatgttggaattcctgatgcggtattttctccttacgcatctgtgcggtat ttcacaccgcatatggtgcactctcagtacaatctgctctgatgccgcatagttaagcca gccccgacacccgccaacacccgctgacgcgccctgacgggcttgtctgctcccggcatc cgcttacagacaagctgtgaccgtctccgggagctgcatgtgtcagaggttttcaccgtc atcaccgaaacgcgcgagacgaaagggcctcgtgatacgcctatttttataggttaatgt catgataataatggtttcttagacgtcaggtggcacttttcggggaaatgtgcgcggaac ccctatttgtttatttttctaaatacattcaaatatgtatccgctcatgagacaataacc ctgataaatgcttcaataatattgaaaaaggaagagtatgagtattcaacatttccgtgt cgcccttattcccttttttgcggcattttgccttcctgttttttgctcacccagaaacgct ggtgaaagtaaaagatgctgaagatcagttgggtgcacgagtgggttacatcgaactgga tctcaacagcggtaagatccttgagagttttcgccccgaagaacgttttccaatgatgag cacttttaaagttctgctatgtggcgcggtattatcccgtattgacgccgggcaagagca
```

-continued

```
actcggtcgccgcatacactattctcagaatgacttggttgagtactcaccagtcacaga aaagcatcttacggatggcatgacagtaagagaattatgcagtgctgccataaccatgag tgataacactgcggccaacttacttctgacaacgatcggaggaccgaaggagctaaccgc tttttgcacaacatgggggatcatgtaactcgccttgatcgttgggaaccggagctgaa tgaagccataccaaacgacgagcgtgacaccacgatgcctgtagcaatggcaacaacgtt gcgcaaactattaactggcgaactacttactctagcttcccggcaacaattaatagactg gatggaggcggataaagttgcaggaccacttctgcgctcggcccttccggctggctggtt tattgctgataaatctggagccggtgagcgtgggtctcgcggtatcattgcagcactggg gccagatggtaagccctcccgtatcgtagttatctacacgacggggagtcaggcaactat ggatgaacgaaatagacagatcgctgagataggtgcctcactgattaagcattggtaact gtcagaccaagtttactcatatatactttagattgatttaaaacttcatttttaatttaa aaggatctaggtgaagatcctttttgataatctcatgaccaaaatcccttaacgtgagtt ttcgttccactgagcgtcagaccccgtagaaaagatcaaaggatcttcttgagatccttt ttttctgcgcgtaatctgctgcttgcaaaaaaaaaaccaccgctaccagcggtggtttgt ttgccggatcaagagctaccaactctttttccgaaggtaactggcttcagcagagcgcag ataccaaatactgtccttctagtgtagccgtagttaggccaccacttcaagaactctgta gcaccgcctacatacctcgctctgctaatcctgttaccagtggctgctgccagtggcgat aagtcgtgtcttaccgggttggactcaagacgatagttaccggataaggcgcagcggtcg ggctgaacggggggttcgtgcacacagcccagcttggagcgaacgacctacaccgaactg agatacctacagcgtgagctatgagaaagcgccacgcttcccgaagggagaaaggcggac aggtatccggtaagcggcagggtcggaacaggagagcgcacgagggagcttccaggggga aacgcctggtatctttatagtcctgtcgggtttcgccacctctgacttgagcgtcgattt ttgtgatgctcgtcaggggggcggagcctatggaaaaacgccagcaacgcggcctttttta cggttcctggccttttgctggccttttgctcacatgttctttcctgcgttatcccctgat tctgtggataaccgtattaccgcctttgagtgagctgataccgctcgccgcagccgaacg accgagcgcagcgagtcagtgagcgaggaagcggaagagcgcccaatacgcaaaccgcct ctccccgcgcgttggccgattcattaatgcagcagctgcgcgctcgctcgctcactgagg ccgcccgggcaaagcccgggcgtcgggcgacctttggtcgcccggcctcagtgagcgagc gagcgcgcagagagggagtggccaactccatcactaggggttccttgtagttaatgatta acccgccatgctacttatctacgtagccatgctctaggacattgattattgactagtgga gttccgcgttacataacttacggtaaatggcccgcctggctgaccgcccaacgacccccg cccattgacgtcaataatgacgtatgttcccatagtaacgccaataagggactttccattg acgtcaatgggtggagtatttacggtaaactgcccacttggcagtacatcaagtgtatca tatgccaagtacgcccccctattgacgtcaatgacggtaaatggcccgcctggcattatgc ccagtacatgaccttatgggactttcctacttggcagtacatctacgtattagtcatcgc tattaccatggtcgaggtgagccccacgttctgcttcactctccccatctcccccccctc cccacccccaattttgtatttatttattttttaattatttttgtgcagcgatggggggggg ggggggggggcgcgcgccaggcggggggggcggggcgagggggggcggggcgaggcgg agaggtgcggcggcagccaatcagagcggcgcgctccgaaagtttccttttatggcgagg cggcggcggcggcgggccctataaaaagcgaagcgcgcggggggggagtcgctgcgcgctg ccttcgccccgtgccccgctccgccgccgcctcgcgccgcccgccccggctctgactgac
```

-continued cgcgttactaaaacaggtaagtccggcctccgcgccgggtttttggcgcctcccgcgggcg cccccctcctcacggcgagcgctgccacgtcagacgaagggcgcagcgagcgtcctgatc cttccgcccggacgctcaggacagcggcccgctgctcataagactcggccttagaacccc agtatcagcagaaggacattttaggacgggacttgggtgactctagggcactggttttct ttccagagagcggaacaggcgaggaaaagtagtcccttctcggcgattctgcggagggat ctccgtggggcggtgaacgccgatgatgcctctactaaccatgttcatgtttttctttttt tttctacaggtcctgggtgacgaacagggtaccgccaccatggccaccggctctcgcaca agcctgctgctggctttcggactgctgtgcctgccttggctccaggagggctccgcc 3'

SEQ ID NO. 2
(miRNA expression cassette No. 2-Bruton's tyrosine kinase):
5' gctagcatcgataccgtcgctatgtgctggaggcttgctgaaggctgtatgctgta aggtggttatgggagaatgccgtttttggcctctgactgacggcattctcctaaccacctt acaggacacaaggcctgttactagcactcacatggaacaaatggcctctagcctggaggc ttgctgaaggctgtatgctgttgagtttcgcattcttgttgccgtttttggcctctgactg acggcaacaagagcgaaactcaacaggacacaaggcctgttactagcactcacatggaac aaatggcctctagcctggaggcttgctgaaggctgtatgctgtctatcctttcaagctag tcaccgtttttggcctctgactgacggtgactagcgaaaggatagacaggacacaaggcct gttactagcactcacatggaacaaatggcctctctagaat 3'

SEQ ID NO. 3 (miRNA expression cassette No. 3-EGFR):

5' gctagcatcgataccgtcgctatgtgctggaggcttgctgaaggctgtatgctgaa gttagcatgtgtcccagaaccgttttggcctctgactgacggttctgggacatgctaact tcaggacacaaggcctgttactagcactcacatggaacaaatggcctctagcctggaggc ttgctgaaggctgtatgctgagaagaaaggtatcccaattgccgtttttggcctctgactg acggcaattgggacctttcttctcaggacacaaggcctgttactagcactcacatggaac aaatggcctctagcctggaggcttgctgaaggctgtatgctgtagtgtttccaaatactg cttgcgtttttggcctctgactgacgcaagcagtatggaaacactacaggacacaaggcct gttactagcactcacatggaacaaatggcctctctagaat 3'

SEQ ID NO. 4 (miRNA expression cassette No. 4-VEGF):
5' gctagcatcgataccgtcgctatgtgctggaggcttgctgaaggctgtatgct gtctgacagtgatgtcatcctttcgttttggcctctgactgacgaaaggatgatcactgt cagacaggacacaaggcctgttactagcactcacatggaacaaatggcctctagcctgga ggcttgctgaaggctgtatgctgatttaggtcagatggaaactcgcgtttttggcctctga ctgacgcgagtttccctgacctaaatcaggacacaaggcctgttactagcactcacatgg aacaaatggcctctagcctggaggcttgctgaaggctgtatgctgagtgtatgcttaacg tggacttcgtttttggcctctgactgacgaagtccacgaagcatacactcaggacacaagg cctgttactagcactcacatggaacaaatggcctctctagaat 3'

SEQ ID NO. 5 (miRNA expression cassette No. 5-BRAF):
5' gctagcatcgataccgtcgctatgtgctggaggcttgctgaaggctgtatgctgata cttcagcctgaatcgtgaccgtttttggcctctgactgacggtcacgattggctgaagtat caggacacaaggcctgttactagcactcacatggaacaaatggcctctagcctggaggct tgctgaaggctgtatgctgacttcactcatattgttccactcgtttttggcctctgactga cgagtggaacaatgagtgaagtcaggacacaaggcctgttactagcactcacatggaaca -continued aatggcctctagcctggaggcttgctgaaggctgtatgctgtatattctacaaatcacca gggcgttttggcctctgactgacgccctggtgatgtagaatatacaggacacaaggcctg ttactagcactcacatggaacaaatggcctctctagaat 3'

SEQ ID NO. 6 (miRNA expression cassette No. 6-ALK):
5' gctagcatcgataccgtcgctatgtgctggaggcttgctgaaggctgtatgctgtat aagtccagtgagaagaaggcgttttggcctctgactgacgccttcttctctggacttata caggacacaaggcctgttactagcactcacatggaacaaatggcctctagcctggaggct tgctgaaggctgtatgctgctatcatcaaatgagctgctgcgttttggcctctgactgac gcagcagctcttgatgatagtcaggacacaaggcctgttactagcactcacatggaacaa atggcctctagcctggaggcttgctgaaggctgtatgctgaagactgctggaaattctat ggctgttttggcctctgactgacgaccatagaatccagcagtctcaggacacaaggcctg ttactagcactcacatggaacaaatggcctctctagaat 3'

SEQ ID NO. 7 (miRNA expression cassette No. 7-HER):
5' gctagcatcgataccgtcgctatgtgctggaggcttgctgaaggctgtatgctgatt agcactggtgatttccggctgttttggcctctgactgacgaccggaaatccagtgctaat caggacacaaggcctgttactagcactcacatggaacaaatggcctctagcctggaggct tgctgaaggctgtatgctgattgagtttcgcattcttgttgccgttttggcctctgactg acggcaacaagagcgaaactcaacaggacacaaggcctgttactagcactcacatggaac aaatggcctctagcctggaggcttgctgaaggctgtatgctgattgatcaggcaaacata gtcccgttttggcctctgactgacgggactatgtgcctgatcaatcaggacacaaggcct gttactagcactcacatggaacaaatggcctctctagaat 3'

SEQ ID NO. 8 (miRNA expression cassette No. 8-FLT3):
5' gctagcatcgataccgtcgctatgtgctggaggcttgctgaaggctgtatgctgtct gatcgtggtgttatttgggcgttttggcctctgactgacgcccaaataaccacgatcaga caggacacaaggcctgttactagcactcacatggaacaaatggcctctagcctggaggct tgctgaaggctgtatgctgttgagtttcgcattcttgttgccgttttggcctctgactga cggcaacaagagcgaaactcaacaggacacaaggcctgttactagcactcacatggaaca aatggcctctagcctggaggcttgctgaaggctgtatgctgtatcctcttataactcagc ctccgttttggcctctgactgacggaggctgagataagaggatacaggacacaaggcctg ttactagcactcacatggaacaaatggcctctctagaat 3'

SEQ ID NO. 9 (miRNA expression cassette No. 9-PARP):
5' gctagcatcgataccgtcgctatgtgctggaggcttgctgaaggctgtatgctgtcg tactgacttgtaggtatgccgttttggcctctgactgacggcatacctaagtcagtacgt caggacacaaggcctgttactagcactcacatggaacaaatggcctctagcctggaggct tgctgaaggctgtatgctgactcctaatcaatagcttccaccgttttggcctctgactga cggtggaagcttgattaggagtcaggacacaaggcctgttactagcactcacatggaaca aatggcctctagcctggaggcttgctgaaggctgtatgctgaatatgcctttaagctttg ctgcgttttggcctctgactgacgcagcaaagcaaaggcatattcaggacacaaggcctg ttactagcactcacatggaacaaatggcctctctagaat 3'

SEQ ID NO: 10 = SEQ ID NO: 1 + SEQ ID NO: 2
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctttatgaggag -continued

```
ttgtggcccgttgtcaggcaacgtggcgtggtgtgcactgtgtttgctgacgcaacccccc actggttggggcattgccaccacctgtcagctcctttccgggactttcgctttcccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctccctttgggccgcctccccgcctaagctt atcgataccgtcgagatctaacttgtttattgcagcttataatggttacaaataaagcaa tagcatcacaaatttcacaaataaagcattttttttcactgcattctagttgtggtttgtc caaactcatcaatgtatcttatcatgtctggatctcgacctcgactagagcatggctacg tagataagtagcatggcgggttaatcattaactacaaggaacccctagtgatggagttgg ccactccctctctgcgcgctcgctcgctcactgaggccgggcgaccaaaggtcgcccgac gcccgggctttgcccgggcggcctcagtgagcgagcgagcgcgcagctggcgtaatagcg aagaggcccgcaccgatcgcccttcccaacagttgcgcagcctgaatggcgaatggcgat tccgttgcaatggctggcggtaatattgttctggatattaccagcaaggccgatagtttg agttcttctactcaggcaagtgatgttattactaatcaaagaagtattgcgacaacggtt aatttgcgtgatggacagactcttttactcggtggcctcactgattataaaaacacttct caggattctggcgtaccgttcctgtctaaaatccctttaatcggcctcctgtttagctcc cgctctgattctaacgaggaaagcacgttatacgtgctcgtcaaagcaaccatagtacgc gccctgtagcggcgcattaagcgcggcgggtgtggtggttacgcgcagcgtgaccgctac acttgccagcgccctagcgcccgctcctttcgctttcttcccttcctttctcgccacgtt cgccggctttccccgtcaagctctaaatcggggggctccctttagggttccgatttagtgc tttacggcacctcgaccccaaaaaacttgattagggtgatggttcacgtagtgggccatc gccctgatagacggtttttcgccctttgacgttggagtccacgttctttaatagtggact cttgttccaaactggaacaacactcaaccctatctcggtctattcttttgatttataagg gattttgccgatttcggcctattggttaaaaaatgagctgatttaacaaaaatttaacgc gaattttaacaaaatattaacgtttacaatttaaatatttgcttatacaatcttcctgtt tttggggcttttctgattatcaaccggggtacatatgattgacatgctagttttacgatt accgttcatcgattctcttgtttgctccagactctcaggcaatgacctgatagcctttgt agagacctctcaaaaatagctaccctctccggcatgaatttatcagctagaacggttgaa tatcatattgatggtgatttgactgtctccggcctttctcacccgtttgaatctttacct acacattactcaggcattgcatttaaaatatatgagggttctaaaaattttttatccttgc gttgaaataaaggcttctcccgcaaaagtattacagggtcataatgtttttggtacaacc gatttagctttatgctctgaggctttattgcttaattttgctaattctttgccttgcctg tatgatttattggatgttggaattcctgatgcggtattttctccttacgcatctgtgcgg tatttcacaccgcatatggtgcactctcagtacaatctgctctgatgccgcatagttaag ccagccccgacacccgccaacacccgctgacgcgccctgacgggcttgtctgctcccggc atccgcttacagacaagctgtgaccgtctccgggagctgcatgtgtcagaggttttcacc gtcatcaccgaaacgcgcgagacgaaagggcctcgtgatacgcctatttttataggttaa tgtcatgataataatggtttcttagacgtcaggtggcacttttcggggaaatgtgcgcgg aaccccatttgtttatttttctaaatacattcaaatatgtatccgctcatgagacaata
```

-continued

```
accctgataaatgcttcaataatattgaaaaaggaagagtatgagtattcaacatttccg tgtcgcccttattcccttttttgcggcattttgccttcctgttttttgctcacccagaaac gctggtgaaagtaaaagatgctgaagatcagttgggtgcacgagtgggttacatcgaact ggatctcaacagcggtaagatccttgagagttttcgccccgaagaacgttttccaatgat gagcactttaaagttctgctatgtggcgcggtattatcccgtattgacgccgggcaaga gcaactcggtcgccgcatacactattctcagaatgacttggttgagtactcaccagtcac agaaaagcatcttacggatggcatgacagtaagagaattatgcagtgctgccataaccat gagtgataacactgcggccaacttacttctgacaacgatcggaggaccgaaggagctaac cgcttttttgcacaacatgggggatcatgtaactcgccttgatcgttgggaaccggagct gaatgaagccataccaaacgacgagcgtgacaccacgatgcctgtagcaatggcaacaac gttgcgcaaactattaactggcgaactacttactctagcttcccggcaacaattaataga ctggatggaggcggataaagttgcaggaccacttctgcgctcggcccttccggctggctg gtttattgctgataaatctggagccggtgagcgtgggtctcgcggtatcattgcagcact ggggccagatggtaagccctcccgtatcgtagttatctacacgacggggagtcaggcaac tatggatgaacgaaatagacagatcgctgagataggtgcctcactgattaagcattggta actgtcagaccaagtttactcatatatactttagattgatttaaaacttcattttaatt taaaaggatctaggtgaagatcctttttgataatctcatgaccaaaatcccttaacgtga gttttcgttccactgagcgtcagacccgtagaaaagatcaaaggatcttcttgagatcc ttttttctgcgcgtaatctgctgcttgcaaacaaaaaaaccaccgctaccagcggtggt ttgtttgccggatcaagagctaccaactctttttccgaaggtaactggcttcagcagagc gcagataccaaatactgtccttctagtgtagccgtagttaggccaccacttcaagaactc tgtagcaccgcctacatacctcgctctgctaatcctgttaccagtggctgctgccagtgg cgataagtcgtgtcttaccgggttggactcaagacgatagttaccggataaggcgcagcg gtcgggctgaacggggggttcgtgcacacagcccagcttggagcgaacgacctacaccga actgagatacctacagcgtgagctatgagaaagcgccacgcttcccgaagggagaaaggc ggacaggtatccggtaagcggcagggtcggaacaggagagcgcacgagggagcttccagg gggaaacgcctggtatctttatagtcctgtcgggtttcgccacctctgacttgagcgtcg atttttgtgatgctcgtcaggggggcggagcctatggaaaaacgccagcaacgcggcctt tttacggttcctggccttttgctggccttttgctcacatgttctttcctgcgttatcccc tgattctgtggataaccgtattaccgcctttgagtgagctgataccgctcgccgcagccg aacgaccgagcgcagcgagtcagtgagcgaggaagcggaagagcgcccaatacgcaaacc gcctctccccgcgcgttggccgattcattaatgcagcagctgcgcgctcgctcgctcact gaggccgcccgggcaaagcccgggcgtcgggcgacctttggtcgcccggcctcagtgagc gagcgagcgcgcagagagggagtggccaactccatcactaggggttccttgtagttaatg attaacccgccatgctacttatctacgtagccatgctctaggacattgattattgactag tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca
```

-continued tcgctattaccatggtcgaggtgagccccacgttctgcttcactctccccatctcccccc cctccccacccccaattttgtatttatttatttttttaattattttgtgcagcgatgggggg ggggggggggggggggcgcgcgccaggcggggggggcggggcgaggggggggcggggcgag gcggagaggtgcggcggcagccaatcagagcggcgcgctccgaaagtttccttttatggc gaggcggcggcggcggcggccctataaaaagcgaagcgcgcggggggggagtcgctgcgc gctgccttcgccccgtgccccgctccgccgccgcctcgcgccgcccgccccggctctgac tgaccgcgttactaaaacaggtaagtccggcctccgcgccgggttttggcgcctcccgcg ggcgccccctcctcacggcgagcgctgccacgtcagacgaagggcgcagcgagcgtcct gatccttccgcccggacgctcaggacagcggcccgctgctcataagactcggccttagaa ccccagtatcagcagaaggacattttaggacgggacttgggtgactctagggcactggtt ttctttccagagagcggaacaggcgaggaaaagtagtcccttctcggcgattctgcggag ggatctccgtggggcggtaacgccgatgatgcctctactaaccatgttcatgttttctt tttttttctacaggtcctgggtgacgaacagggtaccgccaccatggccaccggctctcg cacaagcctgctgctggctttcggactgctgtgcctgccttggctccaggagggctccgc cgctagcatcgataccgtcgctatgtgctggaggcttgctgaaggctgtatgctgtaagg tggttatgggagaatgccgttttggcctctgactgacggcattctcctaaccaccttaca ggacacaaggcctgttactagcactcacatggaacaaatggcctctagcctggaggcttg ctgaaggctgtatgctgttgagtttcgcattcttgttgccgtttttggcctctgactgacg gcaacaagagcgaaactcaacaggacacaaggcctgttactagcactcacatggaacaaa tggcctctagcctggaggcttgctgaaggctgtatgctgtctatcctttcaagctagtca ccgtttttggcctctgactgacggtgactagcgaaaggatagacaggacacaaggcctgtt actagcactcacatggaacaaatggcctctctagaat 3'

SEQ ID NO: 11 = SEQ ID NO: 1 + SEQ ID NO: 3
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctttatgaggag ttgtggcccgttgtcaggcaacgtggcgtggtgtgcactgtgtttgctgacgcaacccccc actggttggggcattgccaccacctgtcagctcctttccgggactttcgctttcccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctcccctttgggccgcctccccgcctaagctt atcgataccgtcgagatctaacttgtttattgcagcttataatggttacaaataaagcaa tagcatcacaaatttcacaaataaagcatttttttcactgcattctagttgtggtttgtc caaactcatcaatgtatcttatcatgtctggatctcgacctcgactagagcatggctacg tagataagtagcatggcgggttaatcattaactacaaggaacccctagtgatggagttgg ccactccctctctgcgcgctcgctcgctcactgaggccgggcgaccaaaggtcgcccgac gcccgggctttgcccgggcggcctcagtgagcgagcgagcgcgcagctggcgtaatagcg aagaggcccgcaccgatcgcccttcccaacagttgcgcagcctgaatggcgaatggcgat tccgttgcaatggctggcggtaatattgttctggatattaccagcaaggccgatagtttg -continued

```
agttcttctactcaggcaagtgatgttattactaatcaaagaagtattgcgacaacggtt aatttgcgtgatggacagactcttttactcggtggcctcactgattataaaaacacttct caggattctggcgtaccgttcctgtctaaaatccctttaatcggcctcctgtttagctcc cgctctgattctaacgaggaaagcacgttatacgtgctcgtcaaagcaaccatagtacgc gccctgtagcggcgcattaagcgcggcgggtgtggtggttacgcgcagcgtgaccgctac acttgccagcgccctagcgcccgctcctttcgctttcttccttcctttctcgccacgtt cgccggctttccccgtcaagctctaaatcgggggctccctttagggttccgatttagtgc tttacggcacctcgaccccaaaaaacttgattagggtgatggttcacgtagtgggccatc gccctgatagacggttttttcgccctttgacgttggagtccacgttctttaatagtggact cttgttccaaactggaacaacactcaaccctatctcggtctattcttttgatttataagg gattttgccgatttcggcctattggttaaaaaatgagctgatttaacaaaaatttaacgc gaattttaacaaaatattaacgtttacaatttaaatatttgcttatacaatcttcctgtt tttggggcttttctgattatcaaccggggtacatatgattgacatgctagttttacgatt accgttcatcgattctcttgtttgctccagactctcaggcaatgacctgatagcctttgt agagacctctcaaaaatagctaccctctccggcatgaatttatcagctagaacggttgaa tatcatattgatggtgatttgactgtctccggcctttctcacccgtttgaatctttacct acacattactcaggcattgcatttaaaatatatgagggttctaaaaatttttatccttgc gttgaaataaaggcttctccccgcaaaagtattacagggtcataatgtttttggtacaacc gatttagctttatgctctgaggctttattgcttaattttgctaattctttgccttgcctg tatgatttattggatgttggaattcctgatgcggtattttctccttacgcatctgtgcgg tatttcacaccgcatatggtgcactctcagtacaatctgctctgatgccgcatagttaag ccagccccgacacccgccaacacccgctgacgcgccctgacgggcttgtctgctcccggc atccgcttacagacaagctgtgaccgtctccgggagctgcatgtgtcagaggttttcacc gtcatcaccgaaacgcgcgagacgaaagggcctcgtgatacgcctattttttataggttaa tgtcatgataataatggtttcttagacgtcaggtggcacttttcggggaaatgtgcgcgg aacccctatttgtttatttttctaaatacattcaaatatgtatccgctcatgagacaata accctgataaatgcttcaataatattgaaaaaggaagagtatgagtattcaacatttccg tgtcgcccttattccctttttttgcggcattttgccttcctgttttttgctcacccagaaac gctggtgaaagtaaaagatgctgaagatcagttgggtgcacgagtgggttacatcgaact ggatctcaacagcggtaagatccttgagagttttcgccccgaagaacgttttccaatgat gagcacttttaaagttctgctatgtggcgcggtattatcccgtattgacgccgggcaaga gcaactcggtcgccgcatacactattctcagaatgacttggttgagtactcaccagtcac agaaaagcatcttacggatggcatgacagtaagagaattatgcagtgctgccataaccat gagtgataacactgcggccaacttacttctgacaacgatcggaggaccgaaggagctaac cgcttttttgcacaacatgggggatcatgtaactcgccttgatcgttgggaaccggagct gaatgaagccataccaaacgacgagcgtgacaccacgatgcctgtagcaatggcaacaac gttgcgcaaactattaactggcgaactacttactctagcttcccggcaacaattaataga ctggatggaggcggataaagttgcaggaccacttctgcgctcggcccttccggctggctg gtttattgctgataaatctggagccggtgagcgtgggtctcgcggtatcattgcagcact ggggccagatggtaagccctcccgtatcgtagttatctacacgacggggagtcaggcaac tatggatgaacgaaatagacagatcgctgagataggtgcctcactgattaagcattggta
```

-continued actgtcagaccaagtttactcatatatactttagattgatttaaaacttcatttttaatt taaaaggatctaggtgaagatccttttttgataatctcatgaccaaaatcccttaacgtga gttttcgttccactgagcgtcagaccccgtagaaaagatcaaaggatcttcttgagatcc ttttttctgcgcgtaatctgctgcttgcaaacaaaaaaaccaccgctaccagcggtggt ttgtttgccggatcaagagctaccaactctttttccgaaggtaactggcttcagcagagc gcagataccaaatactgtccttctagtgtagccgtagttaggccaccacttcaagaactc tgtagcaccgcctacatacctcgctctgctaatcctgttaccagtggctgctgccagtgg cgataagtcgtgtcttaccgggttggactcaagacgatagttaccggataaggcgcagcg gtcgggctgaacggggggttcgtgcacacagcccagcttggagcgaacgacctacaccga actgagatacctacagcgtgagctatgagaaagcgccacgcttcccgaagggagaaaggc ggacaggtatccggtaagcggcagggtcggaacaggagagcgcacgagggagcttccagg gggaaacgcctggtatctttatagtcctgtcgggtttcgccacctctgacttgagcgtcg attttttgtgatgctcgtcaggggggggagcctatggaaaaacgccagcaacgcggcctttt ttacggttcctggccttttgctggccttttgctcacatgttctttcctgcgttatccct gattctgtggataaccgtattaccgcctttgagtgagctgataccgctcgccgcagccga acgaccgagcgcagcgagtcagtgagcgaggaagcggaagagcgcccaatacgcaaaccg cctctccccgcgcgttggccgattcattaatgcagcagctgcgcgctcgctcgctcactg aggccgcccgggcaaagcccgggcgtcgggcgacctttggtcgcccggcctcagtgagcg agcgagcgcgcagagagggagtggccaactccatcactaggggttccttgtagttaatga ttaacccgccatgctacttatctacgtagccatgctctaggacattgattattgactagt ggagttccgcgttacataacttacggtaaatggcccgcctggctgaccgcccaacgaccc ccgcccattgacgtcaataatgacgtatgttcccatagtaacgccaatagggactttcca ttgacgtcaatgggtggagtatttacggtaaactgcccacttggcagtacatcaagtgta tcatatgccaagtacgcccccctattgacgtcaatgacggtaaatggcccgcctggcatta tgcccagtacatgaccttatgggactttcctacttggcagtacatctacgtattagtcat cgctattaccatggtcgaggtgagccccacgttctgcttcactctccccatctcccccc ctccccaccccaattttgtatttatttatttttttaattattttgtgcagcgatggggg gggggggggggggcgcgcgccaggcgggggggcggggcgagggggggcggggcgagg cggagaggtgcggcggcagccaatcagagcggcgcgctccgaaagtttcctttttatggcg aggcggcggcggcggcggccctataaaaagcgaagcgcgcggggggggagtcgctgcgcg ctgccttcgccccgtgccccgctccgccgccgcctcgcgccgcccgccccggctctgact gaccgcgttactaaaacaggtaagtccggcctccgcgccgggttttggcgcctcccgcgg gcgcccccctcctcacggcgagcgctgccacgtcagacgaagggcgcagcgagcgtcctg atccttccgcccggacgctcaggacagcggcccgctgctcataagactcggccttagaac cccagtatcagcagaaggacatttttaggacgggacttgggtgactctagggcactggttt tctttccagagagcggaacaggcgaggaaaagtagtcccttctcggcgattctgcggagg gatctccgtggggcggtgaacgccgatgatgcctctactaaccatgttcatgttttcttt ttttttctacaggtcctgggtgacgaacagggtaccgccaccatggccaccggctctcgc acaagcctgctgctggcttttcggactgctgtgcctgccttggctccaggagggctccgcc gctagcatcgataccgtcgctatgtgctggaggcttgctgaaggctgtatgctgaagtta -continued gcatgtgtcccagaaccgttttggcctctgactgacggttctgggacatgctaacttcag gacacaaggcctgttactagcactcacatggaacaaatggcctctagcctggaggcttgc tgaaggctgtatgctgagaagaaaggtatcccaattgccgttttggcctctgactgacgg caattgggacctttcttctcaggacacaaggcctgttactagcactcacatggaacaaat ggcctctagcctggaggcttgctgaaggctgtatgctgtagtgtttccaaatactgcttg cgttttggcctctgactgacgcaagcagtatggaaacactacaggacacaaggcctgtta ctagcactcacatggaacaaatggcctctctagaat 3'

SEQ ID NO: 12 = SEQ ID NO: 1 + SEQ ID NO: 4
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctcttatgaggag ttgtggcccgttgtcaggcaacgtggcgtggtgtgcactgtgtttgctgacgcaacccccc actggttggggcattgccaccacctgtcagctcctttccgggactttcgctttcccccctc cctattgccacggcggaactcatcgccgcctgccttgcccgctgctggacagggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctcccctttgggccgcctccccgcctaagctt atcgataccgtcgagatctaacttgtttattgcagcttataatggttacaaataaagcaa tagcatcacaaatttcacaaataaagcatttttttcactgcattctagttgtggtttgtc caaactcatcaatgtatcttatcatgtctggatctcgacctcgactagagcatggctacg tagataagtagcatggcgggttaatcattaactacaaggaacccctagtgatggagttgg ccactccctctctgcgcgctcgctcgctcactgaggccgggcgaccaaaggtcgcccgac gcccgggctttgcccgggcggcctcagtgagcgagcgagcgcgcagctggcgtaatagcg aagaggcccgcaccgatcgcccttcccaacagttgcgcagcctgaatggcgaatggcgat tccgttgcaatggctggcggtaatattgttctggatattaccagcaaggccgatagtttg agttcttctactcaggcaagtgatgttattactaatcaaagaagtattgcgacaacggtt aatttgcgtgatggacagactctttttactcggtggcctcactgattataaaaacacttct caggattctggcgtaccgttcctgtctaaaatccctttaatcggcctcctgtttagctcc cgctctgattctaacgaggaaagcacgttatacgtgctcgtcaaagcaaccatagtacgc gccctgtagcggcgcattaagcgcggcgggtgtggtggttacgcgcagcgtgaccgctac acttgccagcgccctagcgcccgctcctttcgctttcttcccttcctttctcgccacgtt cgccggctttccccgtcaagctctaaatcggggggctcccctttagggttccgatttagtgc tttacggcacctcgaccccaaaaaacttgattagggtgatggttcacgtagtgggccatc gccctgatagacggtttttcgccctttgacgttggagtccacgttctttaatagtggact cttgttccaaactggaacaacactcaaccctatctcggtctattcttttgatttataagg gattttgccgatttcggcctattggttaaaaaatgagctgatttaacaaaaatttaacgc gaattttaacaaaatattaacgtttacaatttaaatatttgcttatacaatcttcctgtt tttggggcttttctgattatcaaccggggtacatatgattgacatgctagttttacgatt accgttcatcgattctcttgtttgctccagactctcaggcaatgacctgatagcctttgt agagacctctcaaaaatagctaccctctccggcatgaatttatcagctagaacggttgaa -continued

```
tatcatattgatggtgatttgactgtctccggcctttctcacccgtttgaatctttacct acacattactcaggcattgcatttaaaatatatgagggttctaaaaattttttatccttgc gttgaaataaaggcttctcccgcaaaagtattacagggtcataatgttttttggtacaacc gatttagctttatgctctgaggctttattgcttaattttttgctaattctttgccttgcctg tatgatttattggatgttggaattcctgatgcggtattttctccttacgcatctgtgcgg tatttcacaccgcatatggtgcactctcagtacaatctgctctgatgccgcatagttaag ccagccccgacacccgccaacacccgctgacgcgccctgacgggcttgtctgctcccggc atccgcttacagacaagctgtgaccgtctccgggagctgcatgtgtcagaggttttcacc gtcatcaccgaaacgcgcgagacgaaagggcctcgtgatacgcctattttttataggttaa tgtcatgataataatggtttcttagacgtcaggtggcacttttcggggaaatgtgcgcgg aacccctatttgtttattttttctaaatacattcaaatatgtatccgctcatgagacaata accctgataaatgcttcaataatattgaaaaaggaagagtatgagtattcaacatttccg tgtcgcccttattcccttttttgcggcattttgccttcctgtttttgctcacccagaaac gctggtgaaagtaaaagatgctgaagatcagttgggtgcacgagtgggttacatcgaact ggatctcaacagcggtaagatccttgagagttttcgccccgaagaacgttttccaatgat gagcacttttaaagttctgctatgtggcgcggtattatcccgtattgacgccgggcaaga gcaactcggtcgccgcatacactattctcagaatgacttggttgagtactcaccagtcac agaaaagcatcttacggatggcatgacagtaagagaattatgcagtgctgccataaccat gagtgataacactgcggccaacttacttctgacaacgatcggaggaccgaaggagctaac cgcttttttgcacaacatgggggatcatgtaactcgccttgatcgttgggaaccggagct gaatgaagccataccaaacgacgagcgtgacaccacgatgcctgtagcaatggcaacaac gttgcgcaaactattaactggcgaactacttactctagcttcccggcaacaattaataga ctggatggaggcggataaagttgcaggaccacttctgcgctcggcccttccggctggctg gtttattgctgataaatctggagccggtgagcgtgggtctcgcggtatcattgcagcact ggggccagatggtaagccctcccgtatcgtagttatctacacgacggggagtcaggcaac tatggatgaacgaaatagacagatcgctgagataggtgcctcactgattaagcattggta actgtcagaccaagtttactcatatatactttagattgatttaaaacttcatttttaatt taaaaggatctaggtgaagatcctttttgataatctcatgaccaaaatcccttaacgtga gttttcgttccactgagcgtcagacccccgtagaaaagatcaaaggatcttcttgagatcc ttttttttctgcgcgtaatctgctgcttgcaaacaaaaaaaccaccgctaccagcggtggt ttgtttgccggatcaagagctaccaactctttttccgaaggtaactggcttcagcagagc gcagataccaaatactgtccttctagtgtagccgtagttaggccaccacttcaagaactc tgtagcaccgcctacatacctcgctctgctaatcctgttaccagtggctgctgccagtgg cgataagtcgtgtcttaccgggttggactcaagacgatagttaccggataaggcgcagcg gtcgggctgaacggggggttcgtgcacacagcccagcttggagcgaacgacctacaccga actgagatacctacagcgtgagctatgagaaagcgccacgcttcccgaagggagaaaggc ggacaggtatccggtaagcggcagggtcggaacaggagagcgcacgagggagcttccagg gggaaacgcctggtatctttatagtcctgtcgggtttcgccacctctgacttgagcgtcg attttttgtgatgctcgtcaggggggcggagcctatggaaaaacgccagcaacgcggcctt tttacggttcctggccttttgctggccttttgctcacatgttctttcctgcgttatcccc tgattctgtggataaccgtattaccgcctttgagtgagctgataccgctcgccgcagccg
```

-continued aacgaccgagcgcagcgagtcagtgagcgaggaagcggaagagcgcccaatacgcaaacc gcctctccccgcgcgttggccgattcattaatgcagcagctgcgcgctcgctcgctcact gaggccgcccgggcaaagcccgggcgtcgggcgacctttggtcgcccggcctcagtgagc gagcgagcgcgcagagagggagtggccaactccatcactaggggttccttgtagttaatg attaacccgccatgctacttatctacgtagccatgctctaggacattgattattgactag tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca tcgctattaccatggtcgaggtgagccccacgttctgcttcactctccccatctcccccc cctccccacccccaattttgtatttatttattttttaattattttgtgcagcgatggggg ggggggggggggggcgcgcgccaggcggggggggcggggcgaggggggggcggggcgag gcggagaggtgcggcggcagccaatcagagcggcgcgctccgaaagtttcctttatggc gaggcggcggcggcggcggccctataaaaagcgaagcgcgcggggggggagtcgctgcgc gctgccttcgccccgtgccccgctccgccgccgcctcgcgccgcccgccccggctctgac tgaccgcgttactaaaacaggtaagtccggcctccgcgccgggttttggcgcctcccgcg ggcgccccctcctcacggcgagcgctgccacgtcagacgaagggcgcagcgagcgtcct gatccttccgcccggacgctcaggacagcggcccgctgctcataagactcggccttagaa ccccagtatcagcagaaggacattttaggacgggacttgggtgactctagggcactggtt ttctttccagagagcggaacaggcgaggaaaagtagtcccttctcggcgattctgcggag ggatctccgtggggcggtgaacgccgatgatgcctctactaaccatgttcatgttttctt ttttttctacaggtcctgggtgacgaacagggtaccgccaccatggccaccggctctcg cacaagcctgctgctggctttcggactgctgtgcctgccttggctccaggagggctccgc cgctagcatcgataccgtcgctatgtgctggaggcttgctgaaggctgtatgctgtctga cagtgatgtcatcctttcgttttggcctctgactgacgaaaggatgatcactgtcagaca ggacacaaggcctgttactagcactcacatggaacaaatggcctctagcctggaggcttg ctgaaggctgtatgctgatttaggtcagatggaaactcgcgttttggcctctgactgacg cgagtttccctgacctaaatcaggacacaaggcctgttactagcactcacatggaacaaa tggcctctagcctggaggcttgctgaaggctgtatgctgagtgtatgcttaacgtggact tcgttttggcctctgactgacgaagtccacgaagcatacactcaggacacaaggcctgtt actagcactcacatggaacaaatggcctctctagaat 3'

SEQ ID NO: 13 = SEQ ID NO: 1 + SEQ ID NO: 5
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctttatgaggag ttgtggcccgttgtcaggcaacgtggcgtggtgtgcactgtgtttgctgacgcaacccccc actggttggggcattgccaccacctgtcagctcctttccgggactttcgctttcccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc -continued

```
ctcaatccagcggaccttccttcccgcggcctgctgccggctctgcggcctcttccgcgt cttcgccttcgccctcagacgagtcggatctccctttgggccgcctccccgcctaagctt atcgataccgtcgagatctaacttgtttattgcagcttataatggttacaaataaagcaa tagcatcacaaatttcacaaataaagcattttttttcactgcattctagttgtggtttgtc caaactcatcaatgtatcttatcatgtctggatctcgacctcgactagagcatggctacg tagataagtagcatggggggttaatcattaactacaaggaaccccctagtgatggagttggc cactccctctctgcgcgctcgctcgctcactgaggccgggcgaccaaaggtcgcccgacg cccgggctttgcccgggcggcctcagtgagcgagcgagcgcgcagctggcgtaatagcga agaggcccgcaccgatcgcccttcccaacagttgcgcagcctgaatggcgaatggcgatt ccgttgcaatggctggcggtaatattgttctggatattaccagcaaggccgatagtttga gttcttctactcaggcaagtgatgttattactaatcaaagaagtattgcgacaacggtta atttgcgtgatggacagactcttttactcggtggcctcactgattataaaaacacttctc aggattctggcgtaccgttcctgtctaaaatccctttaatcggcctcctgtttagctccc gctctgattctaacgaggaaagcacgttatacgtgctcgtcaaagcaaccatagtacgcg ccctgtagcggcgcattaagcgcggcgggtgtggtggttacgcgcagcgtgaccgctaca cttgccagcgccctagcgcccgctcctttcgctttcttcccttcctttctcgccacgttc gccggctttccccgtcaagctctaaatcggggggctcccttttagggttccgatttagtgct ttacggcacctcgaccccaaaaaacttgattagggtgatggttcacgtagtgggccatcg ccctgatagacggttttttcgccctttgacgttggagtccacgttctttaatagtggactc ttgttccaaactggaacaacactcaaccctatctcggtctattcttttgatttataaggg attttgccgatttcggcctattggttaaaaaatgagctgatttaacaaaaatttaacgcg aattttaacaaaatattaacgtttacaatttaaatatttgcttatacaatcttcctgttt ttggggcttttctgattatcaaccggggtacatatgattgacatgctagttttacgatta ccgttcatcgattctcttgtttgctccagactctcaggcaatgacctgatagcctttgta gagacctctcaaaaatagctaccctctccggcatgaatttatcagctagaacggttgaat atcatattgatggtgatttgactgtctccggcctttctcacccgtttgaatctttaccta cacattactcaggcattgcatttaaaatatatgagggttctaaaaattttttatccttgcg ttgaaataaaggcttctcccgcaaaagtattacagggtcataatgttttttggtacaaccg atttagctttatgctctgaggctttattgcttaattttgctaattctttgccttgcctgt atgatttattggatgttggaattcctgatgcggtattttctccttacgcatctgtgcggt atttcacaccgcatatggtgcactctcagtacaatctgctctgatgccgcatagttaagc cagccccgacacccgccaacacccgctgacgcgccctgacgggcttgtctgctcccggca tccgcttacagacaagctgtgaccgtctccgggagctgcatgtgtcagaggttttcaccg tcatcaccgaaacgcgcgagacgaaagggcctcgtgatacgcctatttttataggttaat gtcatgataataatggtttcttagacgtcaggtggcacttttcggggaaatgtgcgcgga accccctatttgtttattttttctaaatacattcaaatatgtatccgctcatgagacaataa ccctgataaatgcttcaataatattgaaaaaggaagagtatgagtattcaacatttccgt gtcgcccttattcccttttttgcggcattttgccttcctgtttttgctcacccagaaacg ctggtgaaagtaaaagatgctgaagatcagttgggtgcacgagtgggttacatcgaactg gatctcaacagcggtaagatccttgagagttttcgccccgaagaacgttttccaatgatg
```

-continued

```
agcacttttaaagttctgctatgtggcgcggtattatcccgtattgacgccgggcaagag caactcggtcgccgcatacactattctcagaatgacttggttgagtactcaccagtcaca gaaaagcatcttacggatggcatgacagtaagagaattatgcagtgctgccataaccatg agtgataacactgcggccaacttacttctgacaacgatcggaggaccgaaggagctaacc gctttttttgcacaacatgggggatcatgtaactcgccttgatcgttgggaaccggagctg aatgaagccataccaaacgacgagcgtgacaccacgatgcctgtagcaatggcaacaacg ttgcgcaaactattaactggcgaactacttactctagcttcccggcaacaattaatagac tggatggaggcggataaagttgcaggaccacttctgcgctcggcccttccggctggctgg tttattgctgataaatctggagccggtgagcgtgggtctcgcggtatcattgcagcactg gggccagatggtaagccctcccgtatcgtagttatctacacgacggggagtcaggcaact atggatgaacgaaatagacagatcgctgagataggtgcctcactgattaagcattggtaa ctgtcagaccaagtttactcatatatactttagattgatttaaaacttcattttttaattt aaaaggatctaggtgaagatcctttttgataatctcatgaccaaaatcccttaacgtgag ttttcgttccactgagcgtcagacccgtagaaaagatcaaaggatcttcttgagatcct tttttttctgcgcgtaatctgctgcttgcaaacaaaaaaccaccgctaccagcggtggtt tgtttgccggatcaagagctaccaactcttttttccgaaggtaactggcttcagcagagcg cagataccaaatactgtccttctagtgtagccgtagttaggccaccacttcaagaactct gtagcaccgcctacatacctcgctctgctaatcctgttaccagtggctgctgccagtggc gataagtcgtgtcttaccgggttggactcaagacgatagttaccggataaggcgcagcgg tcgggctgaacggggggttcgtgcacacagcccagcttggagcgaacgacctacaccgaa ctgagatacctacagcgtgagctatgagaaagcgccacgcttcccgaagggagaaaggcg gacaggtatccggtaagcggcagggtcggaacaggagagcgcacgagggagcttccaggg ggaaacgcctggtatctttatagtcctgtcgggtttcgccacctctgacttgagcgtcga tttttgtgatgctcgtcagggggggcggagcctatggaaaaacgccagcaacgcggccttt ttacggttcctggccttttgctggccttttgctcacatgttctttcctgcgttatcccct gattctgtggataaccgtattaccgcctttgagtgagctgataccgctcgccgcagccga acgaccgagcgcagcgagtcagtgagcgaggaagcggaagagcgcccaatacgcaaaccg cctctccccgcgcgttggccgattcattaatgcagcagctgcgcgctcgctcgctcactg aggccgcccgggcaaagcccgggcgtcgggcgacctttggtcgcccggcctcagtgagcg agcgagcgcgcagagagggagtggccaactccatcactaggggttccttgtagttaatga ttaacccgccatgctacttatctacgtagccatgctctaggacattgattattgactagt ggagttccgcgttacataacttacggtaaatggcccgcctggctgaccgcccaacgaccc ccgcccattgacgtcaataatgacgtatgttcccatagtaacgccaatagggactttcca ttgacgtcaatgggtggagtatttacggtaaactgcccacttggcagtacatcaagtgta tcatatgccaagtacgcccccctattgacgtcaatgacggtaaatggcccgcctggcatta tgcccagtacatgaccttatgggactttcctacttggcagtacatctacgtattagtcat cgctattaccatggtcgaggtgagccccacgttctgcttcactctccccatctcccccccc ctccccacccccaattttgtatttatttattttttaattattttgtgcagcgatggggggg gggggggggggggcgcgcgccaggcggggcgggggggcgaggggggggcggggcgagg cggagaggtgcggcggcagccaatcagagcggcgcgctccgaaagtttccttttatggcg aggcggcggcggcggcgcccctataaaaagcgaagcgcgcggggggggagtcgctgcgcg
```

-continued

```
ctgccttcgccccgtgccccgctccgccgccgcctcgcgccgcccgccccggctctgact gaccgcgttactaaaacaggtaagtccggcctccgcgccgggttttggcgcctcccgcgg gcgccccctcctcacggcgagcgctgccacgtcagacgaagggcgcagcgagcgtcctg atccttccgcccggacgctcaggacagcggcccgctgctcataagactcggccttagaac cccagtatcagcagaaggacattttaggacgggacttgggtgactctagggcactggttt tctttccagagagcggaacaggcgaggaaaagtagtcccttctcggcgattctgcggagg gatctccgtggggcggtgaacgccgatgatgcctctactaaccatgttcatgttttcttt tttttctacaggtcctgggtgacgaacagggtaccgccaccatggccaccggctctcgc acaagcctgctgctggctttcggactgctgtgcctgccttggctccaggagggctccgcc gctagcatcgataccgtcgctatgtgctggaggcttgctgaaggctgtatgctgatactt cagcctgaatcgtgaccgttttggcctctgactgacggtcacgattggctgaagtatcag gacacaaggcctgttactagcactcacatggaacaaatggcctctagcctggaggcttgc tgaaggctgtatgctgacttcactcatattgttccactcgttttggcctctgactgacga gtggaacaatgagtgaagtcaggacacaaggcctgttactagcactcacatggaacaaat ggcctctagcctggaggcttgctgaaggctgtatgctgtatattctacaaatcaccaggg cgttttggcctctgactgacgccctggtgatgtagaatatacaggacacaaggcctgtta ctagcactcacatggaacaaatggcctctctagaat 3'
```

SEQ ID NO: 14 = SEQ ID NO: 1 + SEQ ID NO: 6
```
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctctttatgaggag ttgtggcccgttgtcaggcaacgtggcgtggtgtgcactgtgtttgctgacgcaacccccc actggttggggcattgccaccacctgtcagctcctttccgggactttcgctttccccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctcccttttgggccgcctccccgcctaagctt atcgataccgtcgagatctaacttgtttattgcagcttataatggttacaaataaagcaa tagcatcacaaatttcacaaataaagcattttttttcactgcattctagttgtggtttgtc caaactcatcaatgtatcttatcatgtctggatctcgacctcgactagagcatggctacg tagataagtagcatggcgggttaatcattaactacaaggaacccctagtgatggagttgg ccactccctctctgcgcgctcgctcgctcactgaggccgggcgaccaaaggtcgcccgac gcccgggctttgcccgggcggcctcagtgagcgagcgagcgcgcagctggcgtaatagcg aagaggcccgcaccgatcgcccttcccaacagttgcgcagcctgaatggcgaatggcgat tccgttgcaatggctggcggtaatattgttctggatattaccagcaaggccgatagtttg agttcttctactcaggcaagtgatgttattactaatcaaagaagtattgcgacaacggtt aatttgcgtgatggacagactcttttactcggtggcctcactgattataaaaacacttct caggattctggcgtaccgttcctgtctaaaatccctttaatcggcctcctgtttagctcc cgctctgattctaacgaggaaagcacgttatacgtgctcgtcaaagcaaccatagtacgc gccctgtagcggcgcattaagcgcggcgggtgtggtggttacgcgcagcgtgaccgctac
```

-continued acttgccagcgccctagcgcccgctcctttcgctttcttcccttcctttctcgccacgtt cgccggctttccccgtcaagctctaaatcgggggctccctttagggttccgatttagtgc tttacggcacctcgaccccaaaaaacttgattagggtgatggttcacgtagtgggccatc gccctgatagacggtttttcgccctttgacgttggagtccacgttctttaatagtggact cttgttccaaactggaacaacactcaaccctatctcggtctattcttttgatttataagg gattttgccgatttcggcctattggttaaaaaatgagctgatttaacaaaaatttaacgc gaattttaacaaaatattaacgtttacaatttaaatatttgcttatacaatcttcctgtt tttggggcttttctgattatcaaccggggtacatatgattgacatgctagttttacgatt accgttcatcgattctcttgtttgctccagactctcaggcaatgacctgatagcctttgt agagacctctcaaaaatagctaccctctccggcatgaatttatcagctagaacggttgaa tatcatattgatggtgatttgactgtctccggcctttctcacccgtttgaatctttacct acacattactcaggcattgcatttaaaatatatgagggttctaaaaattttttatccttgc gttgaaataaaggcttctcccgcaaaagtattacagggtcataatgttttttggtacaacc gatttagctttatgctctgaggctttattgcttaattttgctaattctttgccttgcctg tatgatttattggatgttggaattcctgatgcggtattttctccttacgcatctgtgcgg tatttcacaccgcatatggtgcactctcagtacaatctgctctgatgccgcatagttaag ccagccccgacacccgccaacacccgctgacgcgccctgacgggcttgtctgctcccggc atccgcttacagacaagctgtgaccgtctccgggagctgcatgtgtcagaggttttcacc gtcatcaccgaaacgcgcgagacgaaagggcctcgtgatacgcctattttttataggttaa tgtcatgataataatggtttcttagacgtcaggtggcacttttcggggaaatgtgcgcgg aacccctatttgtttatttttctaaatacattcaaatatgtatccgctcatgagacaata accctgataaatgcttcaataatattgaaaaaggaagagtatgagtattcaacatttccg tgtcgcccttattcccttttttgcggcattttgccttcctgtttttgctcacccagaaac gctggtgaaagtaaaagatgctgaagatcagttgggtgcacgagtgggttacatcgaact ggatctcaacagcggtaagatccttgagagttttcgccccgaagaacgttttccaatgat gagcacttttaaagttctgctatgtggcgcggtattatcccgtattgacgccgggcaaga gcaactcggtcgccgcatacactattctcagaatgacttggttgagtactcaccagtcac agaaaagcatcttacggatggcatgacagtaagagaattatgcagtgctgccataaccat gagtgataacactgcggccaacttacttctgacaacgatcggaggaccgaaggagctaac cgcttttttgcacaacatgggggatcatgtaactcgccttgatcgttgggaaccggagct gaatgaagccataccaaacgacgagcgtgacaccacgatgcctgtagcaatggcaacaac gttgcgcaaactattaactggcgaactacttactctagcttcccggcaacaattaataga ctggatggaggcggataaagttgcaggaccacttctgcgctcggcccttccggctggctg gtttattgctgataaatctggagccggtgagcgtgggtctcgcggtatcattgcagcact ggggccagatggtaagccctcccgtatcgtagttatctacacgacggggagtcaggcaac tatggatgaacgaaatagacagatcgctgagataggtgcctcactgattaagcattggta actgtcagaccaagtttactcatatatactttagattgatttaaaacttcatttttaatt taaaaggatctaggtgaagatcctttttgataatctcatgaccaaaatcccttaacgtga gttttcgttccactgagcgtcagacccccgtagaaaagatcaaaggatcttcttgagatcc ttttttttctgcgcgtaatctgctgcttgcaaacaaaaaaaccaccgctaccagcggtggt -continued

```
ttgtttgccggatcaagagctaccaactctttttccgaaggtaactggcttcagcagagc gcagataccaaatactgtccttctagtgtagccgtagttaggccaccacttcaagaactc tgtagcaccgcctacatacctcgctctgctaatcctgttaccagtggctgctgccagtgg cgataagtcgtgtcttaccgggttggactcaagacgatagttaccggataaggcgcagcg gtcgggctgaacggggggttcgtgcacacagcccagcttggagcgaacgacctacaccga actgagatacctacagcgtgagctatgagaaagcgccacgcttcccgaagggagaaaggc ggacaggtatccggtaagcggcagggtcggaacaggagagcgcacgagggagcttccagg gggaaacgcctggtatctttatagtcctgtcgggtttcgccacctctgacttgagcgtcg atttttgtgatgctcgtcaggggggcggagcctatggaaaaacgccagcaacgcggcctt tttacggttcctggccttttgctggccttttgctcacatgttctttcctgcgttatcccc tgattctgtggataaccgtattaccgcctttgagtgagctgataccgctcgccgcagccg aacgaccgagcgcagcgagtcagtgagcgaggaagcggaagagcgcccaatacgcaaacc gcctctccccgcgcgttggccgattcattaatgcagcagctgcgcgctcgctcgctcact gaggccgcccgggcaaagcccgggcgtcgggcgacctttggtcgcccggcctcagtgagc gagcgagcgcgcagagagggagtggccaactccatcactaggggttccttgtagttaatg attaacccgccatgctacttatctacgtagccatgctctaggacattgattattgactag tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca tcgctattaccatggtcgaggtgagccccacgttctgcttcactctccccatctccccc cctccccacccccaattttgtatttatttattttttaattattttgtgcagcgatggggg ggggggggggggggcgcgcgccaggcggggggggcggggcgaggggggggcggggcgag gcggagaggtgcggcggcagccaatcagagcggcgcgctccgaaagtttccttttatggc gaggcggcggcggcggcggccctataaaaagcgaagcgcgcggggggggagtcgctgcgc gctgccttcgccccgtgccccgctccgccgccgcctcgcgccgcccgccccggctctgac tgaccgcgttactaaaacaggtaagtccggcctccgcgccgggtttggcgcctcccgcg ggcgccccctcctcacggcgagcgctgccacgtcagacgaagggcgcagcgagcgtcct gatccttccgcccggacgctcaggacagcggcccgctgctcataagactcggccttagaa ccccagtatcagcagaaggacattttaggacgggacttgggtgactctagggcactggtt ttctttccagagagcggaacaggcgaggaaaagtagtcccttctcggcgattctgcggag ggatctccgtggggcggtgaacgccgatgatgcctctactaaccatgttcatgttttctt ttttttctacaggtcctgggtgacgaacagggtaccgccaccatggccaccggctctcg cacaagcctgctgctggctttcggactgctgtgcctgccttggctccaggagggctccgc cgctagcatcgataccgtcgctatgtgctggaggcttgctgaaggctgtatgctgtataa gtccagtgagaagaaggcgttttggcctctgactgacgccttcttctctggacttataca ggacacaaggcctgttactagcactcacatggaacaaatggcctctagcctggaggcttg ctgaaggctgtatgctgctatcatcaaatgagctgctgcgttttggcctctgactgacgc agcagctcttgatgatagtcaggacacaaggcctgttactagcactcacatggaacaaat ggcctctagcctggaggcttgctgaaggctgtatgctgaagactgctggaaattctatgg
```

-continued ctgttttggcctctgactgacgaccatagaatccagcagtctcaggacacaaggcctgtt actagcactcacatggaacaaatggcctctctagaat 3'

SEQ ID NO: 15 = SEQ ID NO: 1 + SEQ ID NO: 7
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctttatgaggag ttgtggcccgttgtcaggcaacgtggcgtggtgtgcactgtgtttgctgacgcaacccccc actggttggggcattgccaccacctgtcagctcctttccgggactttcgctttcccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctcccctttgggccgcctccccgcctaagctt atcgataccgtcgagatctaacttgtttattgcagcttataatggttacaaataaagcaa tagcatcacaaatttcacaaataaagcattttttttcactgcattctagttgtggtttgtc caaactcatcaatgtatcttatcatgtctggatctcgacctcgactagagcatggctacg tagataagtagcatggggggttaatcattaactacaaggaacccctagtgatggagttggc cactccctctctgcgcgctcgctcgctcactgaggccgggcgaccaaaggtcgcccgacg cccgggctttgcccgggcggcctcagtgagcgagcgagcgcgcagctggcgtaatagcga agaggcccgcaccgatcgcccttcccaacagttgcgcagcctgaatggcgaatggcgatt ccgttgcaatggctggcggtaatattgttctggatattaccagcaaggccgatagtttga gttcttctactcaggcaagtgatgttattactaatcaaagaagtattgcgacaacggtta atttgcgtgatggacagactcttttactcggtggcctcactgattataaaaacacttctc aggattctggcgtaccgttcctgtctaaaatccctttaatcggcctcctgtttagctccc gctctgattctaacgaggaaagcacgttatacgtgctcgtcaaagcaaccatagtacgcg ccctgtagcggcgcattaagcgcggcgggtgtggtggttacgcgcagcgtgaccgctaca cttgccagcgccctagcgcccgctcctttcgctttcttcccttcctttctcgccacgttc gccggctttccccgtcaagctctaaatcgggggctccctttagggttccgatttagtgct ttacggcacctcgaccccaaaaaacttgattagggtgatggttcacgtagtgggccatcg ccctgatagacggtttttcgccctttgacgttggagtccacgttctttaatagtggactc ttgttccaaactggaacaacactcaaccctatctcggtctattctttgatttataaggg attttgccgatttcggcctattggttaaaaaatgagctgatttaacaaaaatttaacgcg aattttaacaaaatattaacgtttacaatttaaatatttgcttatacaatcttcctgttt ttggggcttttctgattatcaaccggggtacatatgattgacatgctagttttacgatta ccgttcatcgattctcttgtttgctccagactctcaggcaatgacctgatagcctttgta gagacctctcaaaaatagctaccctctccggcatgaatttatcagctagaacggttgaat atcatattgatggtgatttgactgtctccggcctttctcacccgtttgaatctttaccta cacattactcaggcattgcatttaaaatatatgagggttctaaaaatttttatccttgcg ttgaaataaaggcttctcccgcaaaagtattacagggtcataatgtttttggtacaaccg atttagctttatgctctgaggctttattgcttaattttgctaattctttgccttgcctgt atgatttattggatgttggaattcctgatgcggtattttctccttacgcatctgtgcggt -continued

```
atttcacaccgcatatggtgcactctcagtacaatctgctctgatgccgcatagttaagc cagccccgacacccgccaacacccgctgacgcgccctgacgggcttgtctgctcccggca tccgcttacagacaagctgtgaccgtctccgggagctgcatgtgtcagaggttttcaccg tcatcaccgaaacgcgcgagacgaaagggcctcgtgatacgcctattttttataggttaat gtcatgataataatggtttcttagacgtcaggtggcacttttcggggaaatgtgcgcgga acccctatttgtttattttttctaaatacattcaaatatgtatccgctcatgagacaataa ccctgataaatgcttcaataatattgaaaaaggaagagtatgagtattcaacatttccgt gtcgcccttattccctttttttgcggcattttgccttcctgttttttgctcacccagaaacg ctggtgaaagtaaaagatgctgaagatcagttgggtgcacgagtgggttacatcgaactg gatctcaacagcggtaagatccttgagagttttcgccccgaagaacgttttccaatgatg agcacttttaaagttctgctatgtggcgcggtattatcccgtattgacgccgggcaagag caactcggtcgccgcatacactattctcagaatgacttggttgagtactcaccagtcaca gaaaagcatcttacggatggcatgacagtaagagaattatgcagtgctgccataaccatg agtgataacactgcggccaacttacttctgacaacgatcggaggaccgaaggagctaacc gcttttttgcacaacatgggggatcatgtaactcgccttgatcgttgggaaccggagctg aatgaagccataccaaacgacgagcgtgacaccacgatgcctgtagcaatggcaacaacg ttgcgcaaactattaactggcgaactacttactctagcttcccggcaacaattaatagac tggatggaggcggataaagttgcaggaccacttctgcgctcggcccttccggctggctgg tttattgctgataaatctggagccggtgagcgtgggtctcgcggtatcattgcagcactg gggccagatggtaagccctcccgtatcgtagttatctacacgacggggagtcaggcaact atggatgaacgaaatagacagatcgctgagataggtgcctcactgattaagcattggtaa ctgtcagaccaagtttactcatatatactttagattgatttaaaacttcattttttaattt aaaaggatctaggtgaagatcctttttgataatctcatgaccaaaatcccttaacgtgag ttttcgttccactgagcgtcagacccccgtagaaaagatcaaaggatcttcttgagatcct tttttttctgcgcgtaatctgctgcttgcaaacaaaaaaaccaccgctaccagcggtggtt tgtttgccggatcaagagctaccaactctttttccgaaggtaactggcttcagcagagcg cagataccaaatactgtccttctagtgtagccgtagttaggccaccacttcaagaactct gtagcaccgcctacatacctcgctctgctaatcctgttaccagtggctgctgccagtggc gataagtcgtgtcttaccgggttggactcaagacgatagttaccggataaggcgcagcgg tcgggctgaacggggggttcgtgcacacagcccagcttggagcgaacgacctacaccgaa ctgagatacctacagcgtgagctatgagaaagcgccacgcttcccgaagggagaaaggcg gacaggtatccggtaagcggcagggtcggaacaggagagcgcacgagggagcttccaggg ggaaacgcctggtatctttatagtcctgtcgggtttcgccacctctgacttgagcgtcga tttttgtgatgctcgtcaggggggcggagcctatggaaaaacgccagcaacgcggccttt ttacggttcctggccttttgctggccttttgctcacatgttctttcctgcgttatcccct gattctgtggataaccgtattaccgcctttgagtgagctgataccgctcgccgcagccga acgaccgagcgcagcgagtcagtgagcgaggaagcggaagagcgcccaatacgcaaaccg cctctccccgcgcgttggccgattcattaatgcagcagctgcgcgctcgctcgctcactg aggccgcccgggcaaagcccgggcgtcgggcgacctttggtcgcccggcctcagtgagcg agcgagcgcgcagagagggagtggccaactccatcactagggggttccttgtagttaatga
```

-continued

```
ttaacccgccatgctacttatctacgtagccatgctctaggacattgattattgactagt ggagttccgcgttacataacttacggtaaatggcccgcctggctgaccgcccaacgaccc ccgcccattgacgtcaataatgacgtatgttcccatagtaacgccaatagggactttcca ttgacgtcaatgggtggagtatttacggtaaactgcccacttggcagtacatcaagtgta tcatatgccaagtacgccccctattgacgtcaatgacggtaaatggcccgcctggcatta tgcccagtacatgaccttatgggactttcctacttggcagtacatctacgtattagtcat cgctattaccatggtcgaggtgagccccacgttctgcttcactctccccatctccccccc ctccccacccccaattttgtatttatttattttttaattattttgtgcagcgatgggggg ggggggggggggggcgcgcgccaggcggggcggggggggcgaggggcggggggggcgagg cggagaggtgcggcggcagccaatcagagcggcgcgctccgaaagtttccttttatggcg aggcggcggcggcggcggccctataaaaagcgaagcgcgcggggggggagtcgctgcgcg ctgccttcgccccgtgccccgctccgccgccgcctcgcgccgcccgccccggctctgact gaccgcgttactaaaacaggtaagtccggcctccgcgccgggttttggcgcctcccgcgg gcgcccccctcctcacggcgagcgctgccacgtcagacgaagggcgcagcgagcgtcctg atccttccgcccggacgctcaggacagcggcccgctgctcataagactcggccttagaac cccagtatcagcagaaggacattttaggacgggacttgggtgactctagggcactggttt tctttccagagagcggaacaggcgaggaaaagtagtcccttctcggcgattctgcggagg gatctccgtggggcggtgaacgccgatgatgcctctactaaccatgttcatgtttttcttt ttttttctacaggtcctgggtgacgaacagggtaccgccaccatggccaccggctctcgc acaagcctgctgctggctttcggactgctgtgcctgcccttggctccaggagggctccgcc gctagcatcgataccgtcgctatgtgctggaggcttgctgaaggctgtatgctgattagc actggtgatttccggctgttttggcctctgactgacgaccggaaatccagtgctaatcag gacacaaggcctgttactagcactcacatggaacaaatggcctctagcctggaggcttgc tgaaggctgtatgctgattgagtttcgcattcttgttgccgttttggcctctgactgacg gcaacaagagcgaaactcaacaggacacaaggcctgttactagcactcacatggaacaaa tggcctctagcctggaggcttgctgaaggctgtatgctgattgatcaggcaaacatagtc ccgttttggcctctgactgacgggactatgtgcctgatcaatcaggacacaaggcctgtt actagcactcacatggaacaaatggcctctctagaat 3'
```

SEQ ID NO: 16 = SEQ ID NO: 1 + SEQ ID NO: 8
```
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctttatgaggag ttgtggcccgttgtcaggcaacgtggcgtggtgtgcactgtgtttgctgacgcaacccccc actggttggggcattgccaccacctgtcagctcctttccgggactttcgctttcccccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctcccttgggccgcctccccgcctaagctt atcgataccgtcgagatctaacttgtttattgcagcttataatggttacaaataaagcaa tagcatcacaaatttcacaaataaagcatttttttcactgcattctagttgtggtttgtc
```

-continued

```
caaactcatcaatgtatcttatcatgtctggatctcgacctcgactagagcatggctacg tagataagtagcatggcgggttaatcattaactacaaggaaccccctagtgatggagttgg ccactccctctctgcgcgctcgctcgctcactgaggccgggcgaccaaaggtcgcccgac gcccgggctttgcccgggcggcctcagtgagcgagcgagcgcgcagctggcgtaatagcg aagaggcccgcaccgatcgcccttcccaacagttgcgcagcctgaatggcgaatggcgat tccgttgcaatggctggcggtaatattgttctggatattaccagcaaggccgatagtttg agttcttctactcaggcaagtgatgttattactaatcaaagaagtattgcgacaacggtt aatttgcgtgatggacagactcttttactcggtggcctcactgattataaaaacacttct caggattctggcgtaccgttcctgtctaaaatcccctttaatcggcctcctgtttagctcc cgctctgattctaacgaggaaagcacgttatacgtgctcgtcaaagcaaccatagtacgc gccctgtagcggcgcattaagcgcggcgggtgtggtggttacgcgcagcgtgaccgctac acttgccagcgccctagcgcccgctcctttcgctttcttcccttcctttctcgccacgtt cgccggctttccccgtcaagctctaaatcggggctcccctttagggttccgatttagtgc tttacggcacctcgaccccaaaaaacttgattagggtgatggttcacgtagtgggccatc gccctgatagacggtttttcgcctttgacgttggagtccacgttctttaatagtggact cttgttccaaactggaacaacactcaaccctatctcggtctattcttttgatttataagg gattttgccgatttcggcctattggttaaaaaatgagctgatttaacaaaaatttaacgc gaattttaacaaaatattaacgtttacaatttaaatatttgcttatacaatcttcctgtt tttggggcttttctgattatcaaccggggtacatatgattgacatgctagttttacgatt accgttcatcgattctcttgtttgctccagactctcaggcaatgacctgatagcctttgt agagacctctcaaaaatagctaccctctccggcatgaatttatcagctagaacggttgaa tatcatattgatggtgatttgactgtctccggcctttctcacccgtttgaatctttacct acacattactcaggcattgcatttaaaatatatgagggttctaaaaattttttatccttgc gttgaaataaaggcttctcccgcaaaagtattacagggtcataatgttttttggtacaacc gatttagctttatgctctgaggctttattgcttaattttgctaattctttgccttgcctg tatgatttattggatgttggaattcctgatgcggtattttctccttacgcatctgtgcgg tatttcacaccgcatatggtgcactctcagtacaatctgctctgatgccgcatagttaag ccagccccgacacccgccaacacccgctgacgcgccctgacgggcttgtctgctcccggc atccgcttacagacaagctgtgaccgtctccgggagctgcatgtgtcagaggtttttcacc gtcatcaccgaaacgcgcgagacgaaagggcctcgtgatacgcctatttttataggttaa tgtcatgataataatggtttcttagacgtcaggtggcacttttcggggaaatgtgcgcgg aacccctatttgtttatttttctaaatacattcaaatatgtatccgctcatgagacaata accctgataaatgcttcaataatattgaaaaaggaagagtatgagtattcaacatttccg tgtcgcccttattccctttttttgcggcattttgccttcctgttttttgctcacccagaaac gctggtgaaagtaaaagatgctgaagatcagttgggtgcacgagtgggttacatcgaact ggatctcaacagcggtaagatccttgagagttttcgccccgaagaacgttttccaatgat gagcacttttaaagttctgctatgtggcgcggtattatcccgtattgacgccgggcaaga gcaactcggtcgccgcatacactattctcagaatgacttggttgagtactcaccagtcac agaaaagcatcttacggatggcatgacagtaagagaattatgcagtgctgccataaccat gagtgataacactgcggccaacttacttctgacaacgatcggaggaccgaaggagctaac cgcttttttgcacaacatgggggatcatgtaactcgccttgatcgttgggaaccggagct
```

-continued

```
gaatgaagccataccaaacgacgagcgtgacaccacgatgcctgtagcaatggcaacaac gttgcgcaaactattaactggcgaactacttactctagcttcccggcaacaattaataga ctggatggaggcggataaagttgcaggaccacttctgcgctcggcccttccggctggctg gtttattgctgataaatctggagccggtgagcgtgggtctcgcggtatcattgcagcact ggggccagatggtaagccctcccgtatcgtagttatctacacgacggggagtcaggcaac tatgatgaacgaaatagacagatcgctgagataggtgcctcactgattaagcattggta actgtcagaccaagtttactcatatatactttagattgatttaaaacttcatttttaatt taaaaggatctaggtgaagatcctttttgataatctcatgaccaaaatcccttaacgtga gttttcgttccactgagcgtcagacccgtagaaaagatcaaaggatcttcttgagatcc ttttttctgcgcgtaatctgctgcttgcaaacaaaaaaaccaccgctaccagcggtggt ttgtttgccggatcaagagctaccaactctttttccgaaggtaactggcttcagcagagc gcagataccaaatactgtccttctagtgtagccgtagttaggccaccacttcaagaactc tgtagcaccgcctacatacctcgctctgctaatcctgttaccagtggctgctgccagtgg cgataagtcgtgtcttaccgggttggactcaagacgatagttaccggataaggcgcagcg gtcgggctgaacggggggttcgtgcacacagcccagcttggagcgaacgacctacaccga actgagatacctacagcgtgagctatgagaaagcgccacgcttcccgaagggagaaaggc ggacaggtatccggtaagcggcagggtcggaacaggagagcgcacgagggagcttccagg gggaaacgcctggtatctttatagtcctgtcgggtttcgccacctctgacttgagcgtcg atttttgtgatgctcgtcaggggggcggagcctatggaaaaacgccagcaacgcggcctt tttacggttcctggccttttgctggccttttgctcacatgttctttcctgcgttatcccc tgattctgtggataaccgtattaccgcctttgagtgagctgataccgctcgccgcagccg aacgaccgagcgcagcgagtcagtgagcgaggaagcggaagagcgcccaatacgcaaacc gcctctccccgcgcgttggccgattcattaatgcagcagctgcgcgctcgctcgctcact gaggccgcccgggcaaagcccgggcgtcgggcgacctttggtcgcccggcctcagtgagc gagcgagcgcgcagagagggagtggccaactccatcactaggggttccttgtagttaatg attaacccgccatgctacttatctacgtagccatgctctaggacattgattattgactag tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca tcgctattaccatggtcgaggtgagccccacgttctgcttcactctccccatctccccc cctccccacccccaattttgtatttatttattttttaattattttgtgcagcgatggggg gggggggggggggcgcgcgccaggcggggcggggcggggcgaggggcggggggggcga ggcggagaggtgcggcggcagccaatcagagcggcgcgctccgaaagtttcctttttatgg cgaggcggcggcggcggcggccctataaaaagcgaagcgcgcggggggggagtcgctgcg cgctgccttcgccccgtgccccgctccgccgccgcctcgcgccgcccgcccggctctga ctgaccgcgttactaaaacaggtaagtccggcctccgcgccgggttttggcgcctcccgc gggcgccccctcctcacggcgagcgctgccacgtcagacgaagggcgcagcgagcgtcc tgatccttccgcccggacgctcaggacagcggcccgctgctcataagactcggccttaga
```

-continued

```
accccagtatcagcagaaggacattttaggacgggacttgggtgactctagggcactggt tttctttccagagagcggaacaggcgaggaaaagtagtcccttctcggcgattctgcgga gggatctccgtggggcggtgaacgccgatgatgcctctactaaccatgttcatgttttct tttttttttctacaggtcctgggtgacgaacagggtaccgccaccatggccaccggctctc gcacaagcctgctgctggctttcggactgctgtgcctgccttggctccaggagggctccg ccgctagcatcgataccgtcgctatgtgctggaggcttgctgaaggctgtatgctgtctg atcgtggtgttatttgggcgttttggcctctgactgacgcccaaataaccacgatcagac aggacacaaggcctgttactagcactcacatggaacaaatggcctctagcctggaggctt gctgaaggctgtatgctgttgagtttcgcattcttgttgccgttttggcctctgactgac ggcaacaagagcgaaactcaacaggacacaaggcctgttactagcactcacatggaacaa atggcctctagcctggaggcttgctgaaggctgtatgctgtatcctcttataactcagcc tccgttttggcctctgactgacggaggctgagataagaggatacaggacacaaggcctgt tactagcactcacatggaacaaatggcctctctagaat 3'
```

SEQ ID NO: 17 = SEQ ID NO: 1 + SEQ ID NO: 9
```
5' aatcaacctctggattacaaaatttgtgaaagattgactggtattcttaactatgtt gctccttttacgctatgtggatacgctgctttaatgcctttgtatcatgctattgcttcc cgtatggctttcattttctcctccttgtataaatcctggttgctgtctctttatgaggag ttgtggcccgttgtcaggcaacgtggcgtggtgtgcactgtgtttgctgacgcaacccccc actggttggggcattgccaccacctgtcagctcctttccgggactttcgctttccccctc cctattgccacggcggaactcatcgccgcctgccttgcccgctgctggacaggggctcgg ctgttgggcactgacaattccgtggtgttgtcggggaaatcatcgtcctttccttggctg ctcgcctgtgttgccacctggattctgcgcgggacgtccttctgctacgtcccttcggcc ctcaatccagcggaccttccttcccgcggcctgctgccggctctgcggcctcttccgcgt cttcgccttcgccctcagacgagtcggatctcccctttgggccgcctccccgcctaagctt atcgataccgtcgagatctaacttgtttattgcagcttataatggttacaaataaagcaa tagcatcacaaatttcacaaataaagcattttttttcactgcattctagttgtggtttgtc caaactcatcaatgtatcttatcatgtctggatctcgacctcgactagagcatggctacg tagataagtagcatggcgggttaatcattaactacaaggaacccctagtgatggagttgg ccactccctctctgcgcgctcgctcgctcactgaggccgggcgaccaaaggtcgcccgac gcccgggctttgcccgggcggcctcagtgagcgagcgagcgcgcagctggcgtaatagcg aagaggcccgcaccgatcgcccttcccaacagttgcgcagcctgaatggcgaatggcgat tccgttgcaatggctggcggtaatattgttctggatattaccagcaaggccgatagtttg agttcttctactcaggcaagtgatgttattactaatcaaagaagtattgcgacaacggtt aatttgcgtgatggacagactcttttactcggtggcctcactgattataaaaacacttct caggattctggcgtaccgttcctgtctaaaatccctttaatcggcctcctgtttagctcc cgctctgattctaacgaggaaagcacgttatacgtgctcgtcaaagcaaccatagtacgc gccctgtagcggcgcattaagcgcggcgggtgtggtggttacgcgcagcgtgaccgctac acttgccagcgccctagcgcccgctcctttcgctttcttcccttcctttctcgccacgtt cgccggctttccccgtcaagctctaaatcggggggctcccttttagggttccgatttagtgc tttacggcacctcgaccccaaaaaacttgattagggtgatggttcacgtagtgggccatc gccctgatagacggtttttcgccctttgacgttggagtccacgttctttaatagtggact
```

-continued

```
cttgttccaaactggaacaacactcaaccctatctcggtctattcttttgatttataagg gattttgccgatttcggcctattggttaaaaaatgagctgatttaacaaaaatttaacgc gaattttaacaaaatattaacgtttacaatttaaatatttgcttatacaatcttcctgtt tttggggcttttctgattatcaaccggggtacatatgattgacatgctagttttacgatt accgttcatcgattctcttgtttgctccagactctcaggcaatgacctgatagcctttgt agagacctctcaaaaatagctaccctctccggcatgaatttatcagctagaacggttgaa tatcatattgatggtgatttgactgtctccggcctttctcacccgtttgaatctttacct acacattactcaggcattgcatttaaaatatatgagggttctaaaaatttttatccttgc gttgaaataaaggcttctcccgcaaaagtattacagggtcataatgttttttggtacaacc gatttagctttatgctctgaggctttattgcttaattttgctaattctttgccttgcctg tatgatttattggatgttggaattcctgatgcggtattttctccttacgcatctgtgcgg tatttcacaccgcatatggtgcactctcagtacaatctgctctgatgccgcatagttaag ccagccccgacacccgccaacacccgctgacgcgccctgacgggcttgtctgctcccggc atccgcttacagacaagctgtgaccgtctccgggagctgcatgtgtcagaggttttcacc gtcatcaccgaaacgcgcgagacgaaagggcctcgtgatacgcctatttttataggttaa tgtcatgataataatggtttcttagacgtcaggtggcactttttcggggaaatgtgcgcgg aaccccctatttgtttattttttctaaatacattcaaatatgtatccgctcatgagacaata accctgataaatgcttcaataatattgaaaaaggaagagtatgagtattcaacatttccg tgtcgcccttattcccttttttgcggcattttgccttcctgtttttgctcacccagaaac gctggtgaaagtaaaagatgctgaagatcagttgggtgcacgagtgggttacatcgaact ggatctcaacagcggtaagatccttgagagttttcgccccgaagaacgttttccaatgat gagcacttttaaagttctgctatgtggcgcggtattatcccgtattgacgccgggcaaga gcaactcggtcgccgcatacactattctcagaatgacttggttgagtactcaccagtcac agaaaagcatcttacggatggcatgacagtaagagaattatgcagtgctgccataaccat gagtgataacactgcggccaacttacttctgacaacgatcggaggaccgaaggagctaac cgcttttttgcacaacatgggggatcatgtaactcgccttgatcgttgggaaccggagct gaatgaagccataccaaacgacgagcgtgacaccacgatgcctgtagcaatggcaacaac gttgcgcaaactattaactggcgaactacttactctagcttcccggcaacaattaataga ctggatggaggcggataaagttgcaggaccacttctgcgctcggcccttccggctggctg gtttattgctgataaatctggagccggtgagcgtgggtctcgcggtatcattgcagcact ggggccagatggtaagccctcccgtatcgtagttatctacacgacggggagtcaggcaac tatggatgaacgaaatagacagatcgctgagataggtgcctcactgattaagcattggta actgtcagaccaagtttactcatatatactttagattgatttaaaacttcatttttaatt taaaaggatctaggtgaagatcctttttgataatctcatgaccaaaatcccttaacgtga gttttcgttccactgagcgtcagacccccgtagaaaagatcaaaggatcttcttgagatcc tttttttctgcgcgtaatctgctgcttgcaaacaaaaaaaccaccgctaccagcggtggt ttgtttgccggatcaagagctaccaactctttttccgaaggtaactggcttcagcagagc gcagataccaaatactgtccttctagtgtagccgtagttaggccaccacttcaagaactc tgtagcaccgcctacatacctcgctctgctaatcctgttaccagtggctgctgccagtgg cgataagtcgtgtcttaccgggttggactcaagacgatagttaccggataaggcgcagcg gtcgggctgaacggggggttcgtgcacacagcccagcttggagcgaacgacctacaccga
```

-continued

```
actgagatacctacagcgtgagctatgagaaagcgccacgcttcccgaagggagaaaggc ggacaggtatccggtaagcggcagggtcggaacaggagagcgcacgagggagcttccagg gggaaacgcctggtatctttatagtcctgtcgggtttcgccacctctgacttgagcgtcg atttttgtgatgctcgtcaggggggcggagcctatggaaaaacgccagcaacgcggcctt tttacggttcctggccttttgctggccttttgctcacatgttctttcctgcgttatcccc tgattctgtggataaccgtattaccgcctttgagtgagctgataccgctcgccgcagccg aacgaccgagcgcagcgagtcagtgagcgaggaagcggaagagcgcccaatacgcaaacc gcctctccccgcgcgttggccgattcattaatgcagcagctgcgcgctcgctcgctcact gaggccgcccgggcaaagcccgggcgtcgggcgacctttggtcgcccggcctcagtgagc gagcgagcgcgcagagagggagtggccaactccatcactaggggttccttgtagttaatg attaacccgccatgctacttatctacgtagccatgctctaggacattgattattgactag tggagttccgcgttacataacttacggtaaatggcccgcctggctgaccgcccaacgacc cccgcccattgacgtcaataatgacgtatgttcccatagtaacgccaataggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca tcgctattaccatggtcgaggtgagccccacgttctgcttcactctccccatctccccc cctccccaccccaattttgtatttatttattttttaattattttgtgcagcgatggggg ggggggggggggggcgcgcgccaggcggggcggggcggggcgagggggggggcggggcga ggcggagaggtgcggcggcagccaatcagagcggcgcgctccgaaagtttccttttatgg cgaggcggcggcggcggcggccctataaaaagcgaagcgcgcggggggggagtcgctgcg cgctgccttcgccccgtgccccgctccgccgccgcctcgcgccgcccgccccggctctga ctgaccgcgttactaaaacaggtaagtccggcctccgcgccgggttttggcgcctcccgc gggcgcccccctcctcacggcgagcgctgccacgtcagacgaagggcgcagcgagcgtcc tgatccttccgcccggacgctcaggacagcggcccgctgctcataagactcggccttaga accccagtatcagcagaaggacattttaggacgggacttgggtgactctagggcactggt tttctttccagagagcggaacaggcgaggaaaagtagtcccttctcggcgattctgcgga gggatctccgtggggcggtgaacgccgatgatgcctctactaaccatgttcatgttttct ttttttttctacaggtcctgggtgacgaacagggtaccgccaccatggccaccggctctc gcacaagcctgctgctggctttcggactgctgtgcctgccttggctccaggagggctccg ccgctagcatcgataccgtcgctatgtgctggaggcttgctgaaggctgtatgctgtcgt actgacttgtaggtatgccgttttggcctctgactgacggcatacctaagtcagtacgtc aggacacaaggcctgttactagcactcacatggaacaaatggcctctagcctggaggctt gctgaaggctgtatgctgactcctaatcaatagcttccaccgttttggcctctgactgac ggtggaagcttgattaggagtcaggacacaaggcctgttactagcactcacatggaacaa atggcctctagcctggaggcttgctgaaggctgtatgctgaatatgcctttaagctttgc tgcgttttggcctctgactgacgcagcaaagcaaaggcatattcaggacacaaggcctgt tactagcactcacatggaacaaatggcctctctagaat 3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 10-17 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR. CASI promoter, miRNA expression cassette. WPRE. SV40 polyA and ITR 3'.

The invention claimed is:

1. A composition that comprises a recombinant plasmid (RP) comprising a sequence of nucleotides that is SEQ ID NO: 6.

2. The composition of claim 1, wherein the RP is encapsulated in a protein coat, a lipid vesicle, or any combination thereof.

3. A composition that comprises a recombinant plasmid (RP) comprising a sequence of nucleotides that is SEQ ID NO: 14.

4. The composition of claim 3, wherein the RP is encapsulated in a protein coat, a lipid vesicle, or any combination thereof.

* * * * *